(12) United States Patent
Sterte et al.

(10) Patent No.: US 6,926,882 B2
(45) Date of Patent: Aug. 9, 2005

(54) POROUS INORGANIC MACROSTRUCTURE MATERIALS AND PROCESS FOR THEIR PREPARATION

(75) Inventors: Per Johan Sterte, Lulea (SE); Lubomira Borislavova Tosheva, Luleå (SE)

(73) Assignee: ExxonMobil Chemical Patents Inc., Houston, TX (US)

(*) Notice: Subject to any disclaimer, the term of this patent is extended or adjusted under 35 U.S.C. 154(b) by 0 days.

(21) Appl. No.: 09/755,227

(22) Filed: Jan. 5, 2001

(65) Prior Publication Data

US 2002/0038775 A1 Apr. 4, 2002

Related U.S. Application Data

(60) Provisional application No. 60/174,545, filed on Jan. 5, 2000.

(51) Int. Cl.[7] .......................... C01B 37/00; C01B 39/02
(52) U.S. Cl. ...................... 423/716; 423/702; 423/305; 423/306; 423/DIG. 22; 423/DIG. 24; 423/DIG. 27; 423/335; 423/328.2; 502/60; 502/62; 502/159
(58) Field of Search ................................ 423/700, 702, 423/716, 305, 306, 335, 339, 328.1, 328.2, DIG. 22, DIG. 27, DIG. 24; 502/60, 62, 159

(56) References Cited

U.S. PATENT DOCUMENTS

| | | | |
|---|---|---|---|
| 4,116,858 A | 9/1978 | Lee et al. | 252/184 |
| 4,217,240 A | 8/1980 | Bergna | 252/313 |
| 4,337,171 A | 6/1982 | Kulprathipanja et al. | 252/430 |

(Continued)

FOREIGN PATENT DOCUMENTS

| | | | |
|---|---|---|---|
| EP | 0103035 | 3/1984 | ........... C01D/15/00 |
| EP | 0201264 | 12/1986 | ........... C01B/33/28 |
| EP | 217143 A | * 4/1987 | |

(Continued)

OTHER PUBLICATIONS

Tosheva et al., *Silicalite–1 containing microspheres prepared using shape–directing macro–templates*, Microporous and Mesopoorous Materials, vol. 35–36, Elsevier, pp. 621–629 (Apr. 2000).

(Continued)

*Primary Examiner*—David Sample

(57) ABSTRACT

There is provided macrostructures of porous inorganic material which can have controlled size, shape, and/or porosity and a process for preparing the macrostructures. The macrostructures comprise a three-dimension network of particles of porous inorganic materials. The process for preparing the macrostructures involves forming an admixture containing a porous organic ion exchanger and a synthesis mixture capable of forming a porous inorganic material and then converting the synthesis mixture to a solid porous inorganic material. After formation of the composite material, the porous organic ion exchanger can be removed from the composite material to obtain the macrostructures, either before or after the porous inorganic material is hydrothermally treated with a structure directing agent to convert at least a portion of such porous inorganic material to a crystalline molecular sieve composition. The resulting macrostructure is composed of particles of the crystalline molecular sieve composition.

20 Claims, 9 Drawing Sheets

U.S. PATENT DOCUMENTS

| | | | |
|---|---|---|---|
| 4,670,303 A | | 6/1987 | Miles .................... 427/213.31 |
| 4,680,170 A | * | 7/1987 | Lowe et al. ................ 423/277 |
| 5,399,535 A | | 3/1995 | Whitman ...................... 501/80 |
| 5,916,837 A | | 6/1999 | Harmer et al. .............. 502/170 |
| 6,241,960 B1 | * | 6/2001 | Tops.o slashed.e et al. . 423/305 |

FOREIGN PATENT DOCUMENTS

| | | | | |
|---|---|---|---|---|
| EP | | 260826 | 3/1988 | ............ B01J/35/00 |
| EP | | 0878233 | 11/1998 | ............ B01J/29/00 |
| SE | | 9 802 303 A | 12/1999 | ............ B01J/20/18 |
| WO | | WO82/03571 | 10/1982 | ............ B01J/29/06 |
| WO | | 94-25151 | 11/1994 | ............ B01J/37/00 |
| WO | | WO94/25151 | 11/1994 | ............ B01J/20/18 |
| WO | | WO95/29751 | 11/1995 | ............ B01D/71/02 |
| WO | | WO96/07713 | 3/1996 | ............ C10G/67/00 |
| WO | | 00/00287 | 1/2000 | ............ B01J/47/00 |
| WO | | 00/71254 A1 | 11/2000 | ............ B01J/37/00 |
| WO | | 00/71255 A1 | 11/2000 | ............ B01J/37/00 |

OTHER PUBLICATIONS

Tosheva et al., *Silicalite–1 macrostructures—preparation and structural features, Microporous and Mesoporous Materials*, vol. 39, Elsevier, pp. 91–101 (Sep. 2000).

U.S. Appl. No. 09/315,869, filed May 20, 1999, Per Johan Sterte et al.

U.S. Appl. No. 09/574,433, filed May 20, 2000, Mohr et al.

U.S. Appl. No. 09/574,432, filed May 20, 2000, Mohr et al.

* cited by examiner

POROUS INORGANIC MACROSTRUCTURE MATERIALS AND PROCESS FOR THEIR PREPARATION

This application claims priority to U.S. Provisional Application Ser. No. 60/174,545 filed Jan 5, 2000, which is hereby incorporated by reference.

BACKGROUND OF THE INVENTION

1. Field of the Invention

This invention concerns mesoporous macrostructures composed of a microporous inorganic material which macrostructures can have controlled size, shape, and/or porosity and a process for production of such macrostructures.

2. Description of the Related Art

Both mesoporous inorganic material and microporous inorganic material are characterized by a large specific surface area in pores and are used in a large number of applications of considerable commercial importance. The terms "porous inorganic material" and "porous material", as used herein, includes mesoporous inorganic material, microporous inorganic material, and mixtures or combinations thereof.

In most applications which use porous inorganic material, the fact that the phase interface between the solid porous material and the medium (liquid or gas) in which such use occurs is large can be very important. Heterogeneous phase catalysts used in refinery processes, petrochemical conversion processes, and different environmentally related applications often comprise a use of porous inorganic material, especially microporous material. Adsorbents for the selective adsorption in the gas or liquid phase or the selective separation of ionic compounds are often porous inorganic material. In addition to these applications, porous inorganic materials have recently become increasingly utilized in a number of more technologically advanced areas. Examples of such uses include use in chemical sensors, in fuel cells and batteries, in membranes for separation or catalytic purposes, during chromatography for preparative or analytical purposes, in electronics and optics, and in the production of different types of composites.

Although a large phase interface is often a fundamental requirement for use of porous materials in different applications, a number of additional requirements related to the specific area of application are imposed on these materials. For example, the large phase interface available in the pores of the porous inorganic material must be accessible and useable. Therefore, the porosity, pore size and pore size distribution in large pores (meso- and macropores) are often of major significance, especially when mass transport affects process performance. The surface properties of the porous material can also be very important for the performance of the material in a given application. In this context, the purity of the material comprising the macrostructure is also significant.

In most applications, size and shape of porous macrostructures containing the porous inorganic material and the degree of variation of these properties are very important. During use, the size and shape of the porous macrostructures can influence properties like mass transport within the porous structures, pressure drop over a bed of particles of the macrostructure material, and the mechanical and thermal strength of the macrostructure material. The factors that are the most important will vary, depending on the application in which the macrostructures are used, as well as the configuration of the process in which the application occurs. Techniques that permit production of macrostructure materials with increased specific surface area, pore structure (pore size/pore size distribution), chemical composition, mechanical and thermal strength, as well as increased and uniform size and shape, are consequently required to tailor porous inorganic macrostructures to different applications.

Mesoporous inorganic materials include amorphous metal oxide (non-crystalline) materials which have mesoporous and, optionally, partially microporous structure. The pore size of the mesoporous inorganic material is usually in the range of from about 20 Å to about 500 Å.

Microporous inorganic materials include crystalline molecular sieves. Molecular sieves are characterized by the fact that they are microporous materials with pores of a well-defined size ranging discreetly from about 2 Å to about 20 Å. Most molecules, whether in the gas or liquid phase, both inorganic and organic, have dimensions that fall within this range at room temperature. Selecting a molecular sieve composition with a suitable and discreet pore size therefore allows separation of specific molecules from a mixture with other molecules of a different size through selective adsorption, hence the name "molecular sieve". Apart from the selective adsorption and selective separation of uncharged molecular sieve particles, the well-defined and discreet pore system of a molecular sieve enables selective ion exchange of charged particles and selective catalysis. In the latter two cases, significant properties other than the micropore structure include, for instance, ion exchange capacity, specific surface area and acidity.

Molecular sieves can be classified into various categories such as by their chemical composition and their structural properties. A group of molecular sieves of commercial interest is the group comprising the zeolites, which are defined as crystalline aluminosilicates. Another group is that of the metal silicates, structurally analogous to zeolites, but for the fact that they are substantially free of aluminum (or contain only very small amounts thereof). Still another group of molecular sieves are ALPO-based molecular sieves which contain framework tetrahedral units of alumina ($AlO_2$) and phosphorous oxide ($PO_2$) and, optionally, silica ($SiO_2$). Examples of such molecular sieves include SAPO, ALPO, MeAPO, MeAPSO, ELAPO, and ELAPSO.

A summary of the prior art, in terms of production, modification and characterization of molecular sieves, is described in the book "Molecular Sieves—Principles of Synthesis and Identification"; (R. Szostak, Blackie Academic & Professional, London, 1998, Second Edition). In addition to molecular sieves, amorphous materials, chiefly silica, aluminum silicate and aluminum oxide, have been used as adsorbents and catalyst supports. A number of long-known techniques, like spray drying, prilling, pelletizing and extrusion, have been and are being used to produce macrostructures in the form of, for example, spherical particles, extrudates, pellets and tablets of both micropores and other types of porous materials for use in catalysis, adsorption and ion exchange. A summary of these techniques is described in "Catalyst Manufacture," A. B. Stiles and T. A. Koch, Marcel Dekker, New York, 1995.

Because of limited possibilities with the known techniques to produce macrostructures of amorphous and/or molecular sieve type compositions, considerable investment has been made to find new ways to produce macrostructures of such porous inorganic materials, with a certain emphasis on those in the form of films, with a controllable pore structure together with a requisite mechanical strength of the macrostructure.

PCT Publication WO 94/25151 involves the production of films of molecular sieves by a process in which seed crystals of molecular sieves are deposited on a substrate surface and then made to grow together into a continuous film. PCT Publication WO 94/25152 involves the production of films of molecular sieves by introduction of a substrate to a synthesis solution adjusted for zeolite crystallization and crystallization with a gradual increase in synthesis temperature. PCT Publication WO 94/05597 involves the production of colloidal suspensions of identical microparticles of molecular sieves with an average size below 200 nm. PCT Publication WO 90/09235 involves a method for production of an adsorbent material in the form of a monolith by impregnation of a monolithic cell structure with a hydrophobic molecular sieve, followed by partial sintering of the molecular sieve with the material from which the cell structure is constructed.

Although a number of different techniques already exist for production of porous inorganic macrostructures with the desired size and shape, these techniques have a number of limitations that can affect the properties and performance of the macrostructures during their use. Most of these techniques require the use of an amorphous binder to give the macrostructure acceptable mechanical strength. The presence of the such amorphous binder can adversely affect certain desired properties, such as high specific surface area and uniform chemical composition. Also, most of the existing binding techniques constrain the ability to tailor the macrostructure, in size and shape, within narrow limits. If a well defined size is desired with a narrow particle size distribution, it is many times necessary, and most often required, to separate desirable and undesirable macrostructures, which can lead to considerable waste during manufacture.

The use of different types of binders can also affect the pore structure of the macrostructures and it is often necessary to find a compromise between mechanical properties and pore size. Often it is desirable to have a bimodal pore size distribution in the macrostructures of the porous materials, in which the micropores maintain a large specific phase interface, whereas the larger pores existing in the macrostructure in the meso- or macropore range permit transport of molecules to these microporous surfaces and, in this way, prevent diffusion limitations. During production of macrostructures using the heretofore known techniques, a secondary system of pores within the meso- and/or macropore range can be produced by admixing a particulate inorganic material with an organic material (for example, cellulose fibers), which is later eliminated by calcining. These techniques, however, often produce an adverse effect on the other properties of the resulting macrostructure material.

SUMMARY OF THE INVENTION

The present invention provides a process for the production of macrostructures of porous inorganic materials with controlled size, shape and porosity in which it is possible to overcome or at least mitigate one or more of the above-described problems.

One purpose of this invention is to reduce or eliminate the drawbacks in the known methods for production of macrostructures through a new process which permits production of these macrostructures without addition of binders to produce a uniform final macrostructure composition. Another purpose of this invention is to provide a process, according to which the final shape, size and size distribution of macrostructures composed of molecular sieve particles can be controlled. Still another purpose of this invention is to provide a process according to which both the pore structure of the molecular sieve particle composing the macrostructure and a secondary system of larger pores within the macrostructure can be controlled. A further purpose of this invention is to provide a process for production of macrostructures of porous material with good mechanical and thermal stability.

Accordingly, the present invention first provides a composite material comprising a porous organic ion exchanger and a continuous three-dimensional matrix of porous inorganic material which is present within the three-dimensional pore structure of the porous ion organic ion exchanger. Removal of the porous organic ion exchanger from the composite material results in macrostructures having good mechanical strength and stability. Removal of the organic ion exchanger material from the composite may be performed either before or after the porous inorganic material thereof is treated hydrothermally with a structuring agent to convert it into a crystalline zeolite and/or molecular material.

This invention provides a process for preparing macrostructures of porous inorganic material with controlled size, shape and porosity. The process involves first producing composite material from an admixture containing a porous organic ion exchanger and a synthesis mixture capable of forming a porous inorganic material. In one embodiment of this process the synthesis mixture may contain a structuring agent such that upon its hydrothermal conversion it forms a zeolite and/or molecular sieve composition. In another embodiment of this process, the synthesis mixture may be of a composition that upon hydrothermal treatment converts to an amorphous metal oxide which, before or after removal of the organic ion exchanger, upon a further hydrothermal treatment in the presence of a structuring agent then converts to a zeolite and/or molecular sieve composition. After formation of the composite material, the porous organic ion exchanger is removed from the composite material to obtain the macrostructures.

Also in accordance with the present invention, there is provided a process for the conversion of a hydrocarbon feed which uses a catalyst comprised of porous macrostructures of porous inorganic material which can have controlled size, shape and porosity and comprise a three-dimensional network of particles of porous inorganic material.

The present invention provides a process for the conversion of a hydrocarbon feed using a catalyst comprised of macrostructures of porous inorganic material made by a process which comprises the steps of (a) forming an admixture comprising a porous organic ion exchanger and a synthesis mixture capable of forming said porous inorganic material and which occupies at least a portion of the pore space of the porous organic ion exchanger; (b) converting said synthesis mixture within the pore space of said porous organic ion exchanger under hydrothermal conditions to form said porous inorganic material; and, (c) removing said porous organic ion exchanger.

Examples of specific hydrocarbon conversion processes where the catalyst finds application include catalytic cracking, alkylation, dealkylation, dehydrogenation, disproportionation, transalkylation, hydrocracking, isomerization, dewaxing, oligomerization, and reforming processes.

The process of this invention provides macrostructures of porous inorganic material which can have controlled size, shape and porosity and comprise a three-dimensional network of particles of porous inorganic material.

DETAILED DESCRIPTION OF THE INVENTION

Figure 1:
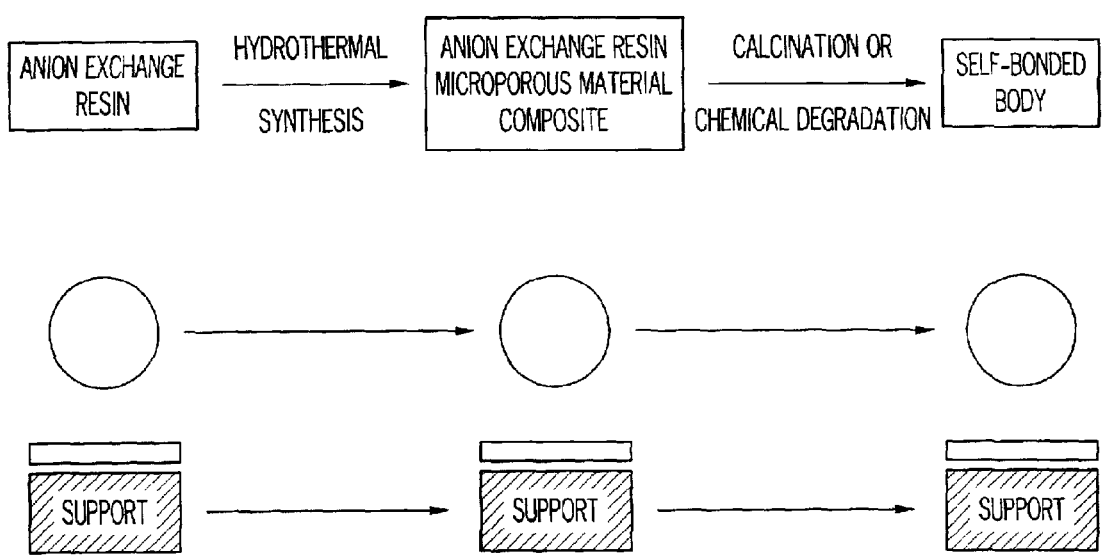
FIG. 1 represents a schematic description of the different stages in production of spherical particles or thin films of porous organic material according to the invention.

The process of the present invention for preparing of macrostructures of porous inorganic material preferably comprises the following steps:

(a) forming an admixture comprising a porous organic ion exchanger and a synthesis mixture capable of forming said porous inorganic material and which occupies at least a portion of the pore space of the porous organic ion exchanger;

(b) converting said synthesis mixture within the pore space of said porous organic ion exchanger under hydrothermal conditions to form said porous inorganic material; and, (c) removing said porous organic ion exchanger.

The porous organic ion exchanger can be removed using techniques know to persons skilled in the art. Examples of such techniques include oxidation processes such as calcination, and chemical removal such as by chemical destruction or chemical dissolution. Usually, the removal of the porous organic ion exchanger will result in macrostructures the mesoporous structure of which have a size and shape that is dictated by the employed organic ion exchanger. The macrostructure is composed of particles of the inorganic material the micropores of which are a function the synthesis mixture used to impregnate the organic ion exchanger and the hydrothermal treatment conditions employed for conversion of the synthesis mixture while within the pore volume of the organic ion exchanger.

As experience has so far established, this invention both in terms of the macrostructure produced and/or the method of its production is applicable with any synthesis composition heretofore disclosed for a production of an amorphous meso- and/or macroporous particles or for a production of microporous particles, which particles in turn comprise the macrostructures of this invention. This is very advantageous in respect to the handling/use properties of a composition composed of macrostructures where the chemical properties thereof are primarily dictated by the characteristics of microcrystals of which the macrostructures are composed.

Macrostructures refer to structures with a size that exceeds 0.01 mm in at least one dimension, preferably 0.1 mm and, more preferably, 1.0 mm. Examples of macrostructures are spherical particles, cylindrical extrudates, pellets, fibers, thin films applied to different forms of substrates and other composites, in which the porous material is combined with other types of material.

The term "average particle size" as used herein, means the arithmetic average of the diameter distribution of the particles on a volume basis.

The macrostructure will be porous and will comprise a three-dimensional matrix of particles of porous inorganic oxide. Usually, the particles will occupy less than 75% of the volume of the macrostructures. Preferably, the inorganic oxide particles will have an average particle size of less than 500 nm. The particles will be joined together and can even be intergrown. More preferably, the particles will have an average particle size of less than 200 nm, e.g., 100 nm and will occupy less than 50% of the total volume of the macrostructure.

Porous inorganic materials that find particular application include crystalline molecular sieves and mesoporous materials. Examples of mesoporous material that find particular application include amorphous silica, amorphous alumina, and amorphous aluminosilicates. For some applications, it is preferable that the pore size of the mesoporous inorganic material be in the range of from about 20 Å to about 50 Å.

Where the composite (organic ion exchanger impregnated with unconverted or converted synthesis mixture) and/or macrostructure (i.e., the structure remaining after removal of the organic ion exchanger) is prepared from a synthesis mixture that upon hydrothermal conversion yields a mesoporous inorganic material—such as an amorphous silica and/or aluminosilicate—the inorganic material of the composite and/or macrostructure may be converted to a zeolite and/or molecular sieve composition by a hydrothermal treatment in the presence of a structure directing agent.

Molecular sieves produced by the process of the invention include silicates, metallosilicates such as aluminosilicates and gallosilicates, and ALPO-based molecular sieves such as alumino-phosphates (ALPO), silicoaluminophosphates (SAPO), metalloalumino-phosphates (MeAPO), and metalloaluminophosphosilicate (MeAPSO). Some of these molecular sieves, while not being true zeolites, are frequently referred to in the literature as such, and this term will be used broadly below.

Molecular sieves/zeolites that find application in the present invention include any of the naturally occurring or synthetic crystalline molecular sieves. Examples of these zeolites include large pore zeolites, intermediate pore size zeolites, and small pore zeolites. These zeolites and their isotypes are described in "Atlas of Zeolite Structure Types", eds. W. H. Meier, D. H. Olson and Ch. Baerlocher, Elsevier, Fourth Edition, 1996, which is hereby incorporated by reference. A large pore zeolite generally has a pore size of at least about 7 Å and includes LTL, VFI, MAZ, MEI, FAU, EMT, OFF, *BEA, and MOR structure type zeolites (IUPAC Commission of Zeolite Nomenclature). Examples of large pore zeolites include mazzite, offretite, zeolite L, VPI-5, zeolite Y, zeolite X, omega, Beta, ZSM-3, ZSM-4, ZSM-18, ZSM-20, SAPO-37, and MCM-22. An intermediate pore size zeolite generally has a pore size from about 5 Å to about 7 Å and includes, for example, MFI, MEL, MTW, EUO, MTT, MFS, AEL, AFO, HEU, FER, and TON structure type zeolites (IUPAC Commission of Zeolite Nomenclature). Examples of intermediate pore size zeolites include ZSM-5, ZSM-11, ZSM-12, ZSM-22, ZSM-23, ZSM-34, ZSM-35, ZSM-48, ZSM-50, ZSM-57, silicalite 1, and silicalite 2. A small pore size zeolite has a pore size from about 3 Å to about 5.0 Å and includes, for example, CHA, ERI, KFI, LEV, SOD, and LTA structure type zeolites (IUPAC Commission of Zeolite Nomenclature). Examples of small pore zeolites include ZK-4, ZSM-2, SAPO-34, SAPO-35, ZK-14, SAPO-42, ZK-21, ZK-22, ZK-5, ZK-20, zeolite A, hydroxysodalite, erionite, chabazite, zeolite T, gemlinite, ALPO-17, and clinoptilolite.

The preferred molecular sieve/zeolite will depend on its use. There are many known ways to tailor the properties of the molecular sieves, for example, structure type, chemical composition, ion-exchange, and activation procedures. Macrostructures comprised of molecular sieve particles do not require the presence of significant amounts of amorphous materials to bind together the molecular sieve particles. Thus, macrostructures comprised of the molecular sieve particles can contain less than 10% by weight of amorphous binder material based on the weight of the microstructures. For many applications, these macrostructures will contain even lesser amounts of amorphous binder, e.g., 5% by weight or even less, e.g., the macrostructures can be substantially free of amorphous binder.

When the molecular sieve produced is an crystalline metallosilicate, the chemical formula of such an anhydrous crystalline metallosilicate can be expressed in terms of moles as represented by the formula:

$$M_{2/n}O:W_2O_3:ZSiO_2,$$

wherein M is selected from the group consisting of hydrogen, hydrogen precursors, monovalent, divalent, and trivalent cations and mixtures thereof; n is the valence of the cation and Z is a number of at least 2, preferably at least 3, said value being dependent upon the particular type of molecular sieve, and W is a metal in the anionic framework structure of the molecular sieve such as aluminum, gallium, boron, or iron.

When the molecular sieve produced has an intermediate pore size, the molecular sieve preferably comprises a composition having the following molar relationship:

$$X_2O_3:(n)YO_2,$$

wherein X is a trivalent element, such as aluminum, gallium, zinc, iron, and/or boron, Y is a tetravalent element such as silicon, tin, and/or germanium; and n has a value greater than 10, usually from about 20 to less than 20,000, more usually from 50 to 2,000, said value being dependent upon the particular type of molecular sieve and the trivalent element present in the molecular sieve.

When the molecular sieve is a gallosilicate intermediate pore size molecular sieve, the molecular sieve preferably comprises a composition having the following molar relationship:

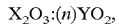
$$Ga_2O_3:ySiO_2$$

wherein y is between about 20 and about 500, typically from 20 to 200. The molecular sieve framework may contain only gallium and silicon atoms or may also contain a combination of gallium, aluminum, and silicon.

The composition of the synthesis mixture will vary according to the porous inorganic material to be produced. For example, in making silicalite 1 or silicalite 2, the aqueous synthesis mixture will contain a source of silicon, and will usually contain a structure directing agent. When preparing an aluminosilicate zeolite, the aqueous synthesis mixture will contain sources of silica and alumina and will usually contain a structure directing agent. When the porous inorganic material to be produced is an ALPO-based molecular sieve, the aqueous synthesis mixture will contain sources of aluminum and phosphorus, optionally silicon and will usually contain a structure directing agent.

For the manufacture of a MFI structure type zeolite, especially ZSM-5 or silicalite 1, the synthesis mixture is advantageously of a molar composition, calculated in terms of oxides, within the following ranges:

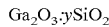

| | |
|---|---|
| $M_2O:SiO_2$ | 0 to 0.7 to :1, preferably 0.016 to 0.350:1 |
| $SiO_2:Al_2O_3$ | 12 to infinity :1 |
| $(TPA)_2O:SiO_2$ | 0 to 0.2:1, preferably 0 to 0.075:1 |
| $H_2O:SiO_2$ | 7 to 1000:1, preferably 9 to 300:1 | wherein TPA represents tetrapropylammonium and M is an alkali metal, preferably sodium or potassium, also Li, Cs and ammonia. Other template agents may be used in these ratios.

The organic ionic exchangers used in the present invention refers to organic porous materials with a surface charge and ion exchange capacity for anions or cations. Preferably, the organic ionic exchangers are polymer-based which are sometimes referred to as ion exchange resins. Polymer-based ionic exchangers are commercially available or can be readily prepared from resins that are commercially available. Examples of such resins include resins sold by Rohm and Haas Company under the registered trademark Amberlyst and resins sold by the Dow Chemical Company under the registered trademark Dowex. These exchangers cover a broad spectrum of different cation and anion exchangers with varying ion exchange capacity, porosity, pore size and particle size. Ion exchangers with an apparent anion exchange capacity, typically greater than about 1 meg/gm of dry anion exchanger, are of special interest to the present invention. Macroreticular organic ionic exchangers are particularly preferred in the practice of the present invention. By "macroreticular," as the term is commonly used in the resin art, it is generally meant that the pores, voids, or reticules are substantially within the range of about 200 to about 2,000 Å. Macroreticular resins are also referred to as macroporous resins.

A preferred group of ion exchangers suitable for use in the process of the present invention are anion exchange resins comprising water-insoluble polymeric resins having attached thereto a plurality of active anion exchange sites. The resin generally contains sufficient of such active ion exchange groups to impart thereto a concentration of ion exchange sites in the range from about 0.5 to about 12 meq/gram dry resin, typically greater than 1 meg/gram, and in some cases, preferably from about 4 to about 5.5 meq/gram of dry resin.

Anion-exchange resins are characterized as either strong base or weak base anion-exchange resins depending on the active ion-exchange sites of the resin. Strong base anion-exchange resins consist of polymers having mobile monovalent anions, such as hydroxide and the like associated, for example, with covalently bonded quaternary ammonium, phosphonium or arsonium functional groups or tertiary sulfonium functional groups. These functional groups are known as active sites and are distributed over the surface of the resin particle. Strong base anion-exchange resins have the capacity to undergo ion exchange independent of the pH of the medium by virtue of their intrinsic ionic character. Macroreticular strong base anion-exchange resins in the hydroxide form are particularly preferred in the practice of the present invention.

The resin matrix of weak base anion-exchange resins contains chemically bonded thereto a basic, nonionic functional group. The functional groups include primary, secondary, or tertiary amine groups. These may be aliphatic, aromatic, heterocyclic or cycloalkane amine groups. They may also be diamine, triamine, or alkanolamine groups. The amines, for example, may include alpha, alpha-dipyridyl, guanidine, and dicyanodiamidine groups. Other nitrogen-containing basic, non-ionic functional groups include nitrile, cyanate, isocyanate, thiocyanate, isothiocyanate, and isocyanide groups. Pyridine groups may also be employed.

Ion exchangers of the strongly basic type which contain quaternary ammonium groups, have been found to be particularly suited for use in the present invention. Commercially available ion exchangers are generally in the form of spherical particles with a relatively narrow particle size distribution. Organic ion exchangers with a size and shape other than spherical, for example, fibers or flakes, however, can be produced according to known techniques. It is also known that films of organic ion exchangers can be deposited on different forms of substrates.

The term "seeds" refers to particles, e.g., crystallites, of porous inorganic material, e.g., molecular sieves, that are capable of initiating crystallization of the desired porous inorganic material. The seeds can be present in the synthesis mixture before its synthesis, e.g., seeds can be added to the synthesis mixture, or can be formed in situ usually in the early stage of synthesis of the porous inorganic material. By treatment of the synthesis mixture with appropriate concentration and under suitable conditions, the seeds can be made to grow and form a continuous structure in the pore system of the ion exchanger. Examples of such seeds includes silicate seeds, metal silicate seeds such as aluminosilicate, borosilicate, gallosilicate, and iron silicate seeds, SAPO seeds, and ALPO seeds. Preferred seeds include olgomeric anions of silicates and metal silicates. The term "seeds" also includes microcrystals of porous inorganic material, e.g., crystals of molecular sieves with a size below 500 nm, e.g., 200 nm, and whose crystal structure can be identified by X-ray diffraction. Microcrystals of molecular sieves suitable for use in the process of the present invention are disclosed in U.S. Pat. No. 5,863,516, which is hereby incorporated by reference.

Although the invention is not intended to be limited to any theory of operation, it is believed that one of the advantages of the present invention is that the surface of the porous organic ion exchanger can facilitate nucleation of the synthesis mixture resulting in the formation of seeds which can subsequently grow into a porous inorganic matrix. In line with this theory, it is believed that the surface charge of the porous organic ion exchanger can attract seeds or seed forming material onto the surface of the porous the ion exchanger. For example, anion exchange resins, which have a positive charge, can attract negatively charged seeds such as silicate seeds, metal silicate seeds and aluminosilicate seeds.

In a second phase in a production of porous macrostructures according to the invention, such seeds formed on or bonded to the surface in the organic ion exchanger are made to grow such as by hydrothermal treatment in an appropriate synthesis solution. Through this growth a continuous three-dimensional network of porous material is formed within the pore structure of the employed organic ion exchange structure. After this stage, the product is a composite material comprising two continuous three-dimensional networks, one comprising the polymer structure of the organic ion exchanger, and the second comprising the formed inorganic porous material. Introduction of seeds can be carried out physically in a separate stage, with a subsequent growth stage under appropriate conditions in a synthesis solution. However, it is also possible and often advantageous not to separate these stages, but instead to directly introduce the ion exchanger material into a synthesis solution and expose this to hydrothermal conditions, during which seeds are formed in or ion-exchanged from the synthesis solution to the ion exchanger, to then grow the material into a continuous structure.

Molecular sieves are generally produced by hydrothermal treatment of a silicate solution with synthesis mixture. Hydrothermal treatment refers to treatment in aqueous solution or aqueous suspension at a temperature exceeding 50° C., preferably exceeding 80° C. and, in most cases, exceeding 95° C. In some instances, it is preferable to carry out the hydrothermal treatment first at a lower temperature and then at a higher temperature. In the synthesis of some of the microporous molecular sieves, e.g., silicalite 1, the crystallinity can be increased when the hydrothermal treatment is carried out at in two steps. In the initial step, the temperature is lower, e.g., 90–110° C., than the second step, e.g., 150–165° C.

The composition of the synthesis mixture and the synthesis parameters, like temperature, time and pressure, can effect the product obtained as well as the size and shape of the formed crystals. This applies both in syntheses, in which the final product is deposited as crystals in the porous structure of an organic ion exchanger, and in conventional synthesis, when the final crystal size is most often much larger. The material deposited in the pore system of the organic ion exchanger is therefore dependent on the composition of the synthesis mixture and the synthesis conditions. During crystallization of macrostructures of a given molecular sieve according to the present invention, it is sometimes desirable to use synthesis mixtures, which, in the absence of ion exchanger material, result in colloidal suspensions of the desired molecular sieve. In some instances, the organic ion exchanger material can influence the result of the synthesis.

The composite of organic ion exchanger and porous inorganic material obtained after this process can be of interest by itself in certain commercial applications. However, for most potential areas of application it is advantageous to eliminate the organic ion exchanger from the composite. This can occur after formation of the porous inorganic material, which leaves behind only the porous inorganic material with a secondary pore system with a porosity and pore size caused by the structure of the employed organic ion exchanger. Removal of the organic ion exchanger preferably occurs by calcining at a temperature exceeding 400° C. The calcination can take place in the presence of acid, in which this material is burned to mostly carbon dioxide and water. As an alternative, the organic material can be removed by selective dissolution with a solvent that dissolves the ion exchanger, but not the inorganic material, or with selective decomposition of the organic material by means of a chemical reaction other than by an oxidation reaction.

After removal of the organic ion exchanger, the resulting inorganic macrostructure is usually a replica in size and shape of the organic ion exchanger present in the admixture.

This means that the possibilities for controlling the size, shape and meso/macroporosity in the inorganic porous material are largely determined by the possibilities of structural manipulation of the properties of the organic ion exchanger. The secondary pore structure of the macrostructure will be revealed following removal of the organic ion exchanger material. The macrostructure however, can be further treated after removal from the organic ion exchanger. In one case, wherein the remaining organic material of the macrostructure is an amorphous silica and/or aluminosilicate, this macrostructure be subjected to another hydrothermal treatment in a solution of an appropriate compositional make-up to convert the amorphous inorganic material into a zeolite and/or molecular sieve material. In another case wherein the synthesis mixture within the pore volume of the organic ion exchanger is of a composition that converts to a zeolite and/or molecular sieve upon the initial hydrothermal treatment, then the macrostructure left after removal of the organic ion exchanger may be treated to cause a deposition thereon of porous inorganic materials, e.g., molecular sieves such as silicalite 1 and silicalite 2. Upon depositing the inorganic material, the secondary pore structure can be more or less sealed and, in the extreme case, to leave behind a homogeneous porous material (without porosity in the meso/macropore range). This could be of interest, for example, in the production of thin films of porous structures, for use in applications like membranes for catalyst or separation purposes, or in chemical sensors. It is also possible, according to a known technique, to coat the surface of the macrostructures of a given type of porous inorganic material produced according to the invention with a thin film of another type of material, something that could be of interest in a catalytic context or during use of macrostructures for controlled dosage of drugs or pesticides.

The porous inorganic material prepared by the process of the present invention can be treated to provide a more acidic form or to replace at least in part the original metals present in the materials with a different cation, e.g., a Group IB to VIII Periodic Table metal such as nickel, copper, zinc, palladium, platinum, calcium or rare earth metal. Thereafter these materials may be used as catalyst in hydrocarbon conversion processes.

The hydrocarbon conversion processes are used for processing hydrocarbon feedstocks. Hydrocarbon feedstocks contain carbon compounds and can be from many different sources, such as virgin petroleum fractions, recycle petroleum fractions, tar sand oil, and, in general, can be any carbon containing fluid susceptible to zeolitic catalytic reactions. Depending on the type of processing the hydrocarbon feed is to undergo, the feed can contain metal or can be free of metals. Also, the feed can also have high or low nitrogen or sulfur impurities.

The conversion of hydrocarbon feeds can take place in any convenient mode, for example, in fluidized bed, moving bed, or fixed bed reactors depending on the types of process desired.

Examples of hydrocarbon compound conversion processes that find application in the process of the present invention include, as non-limiting examples, the following:

(A) The catalytic cracking of a naphtha feed to produce light olefins. Typical reaction conditions include from about 500° C. to about 750° C., pressures of subatmospheric or atmospheric, generally ranging up to about 10 atmospheres (gauge) and residence time (volume of the catalyst, feed rate) from about 10 milliseconds to about 10 seconds.

(B) The catalytic cracking of high molecular weight hydrocarbons to lower weight hydrocarbons. Typical reaction conditions for catalytic cracking include temperatures of from about 400° C. to about 700° C., pressures of from about 0.1 atmosphere (bar) to about 30 atmospheres, and weight hourly space velocities of from about 0.1 to about 100 hr−1.

(C) The transalkylation of aromatic hydrocarbons in the presence of polyalkylaromatic hydrocarbons. Typical reaction conditions include a temperature of from about 200° C. to about 500° C., a pressure of from about atmospheric to about 200 atmospheres, a weight hourly space velocity of from about 1 to about 100 hr−1 and an aromatic hydrocarbon/polyalkylaromatic hydrocarbon mole ratio of from about 0.5/1 to about 16/1.

(D) The isomerization of aromatic (e.g., xylene) feedstock components. Typical reaction conditions for such include a temperature of from about 230° C. to about 510° C., a pressure of from about 0.5 atmospheres to about 50 atmospheres, a weight hourly space velocity of from about 0.1 to about 200 hr−1 and a hydrogen/hydrocarbon mole ratio of from about 0 to about 100.

(E) The dewaxing of hydrocarbons by selectively removing straight chain paraffins. The reaction conditions are dependent in large measure on the feed used and upon the desired pour point. Typical reaction conditions include a temperature between about 200° C. and 450° C., a pressure up to 3,000 psig and a liquid hourly space velocity from 0.1 to 20.

(F) The alkylation of aromatic hydrocarbons, e.g., benzene and alkylbenzenes, in the presence of an alkylating agent, e.g., olefins, formaldehyde, alkyl halides and alcohols having 1 to about 20 carbon atoms. Typical reaction conditions include a temperature of from about 100° C. to about 500° C., a pressure of from about atmospheric to about 200 atmospheres, a weight hourly space velocity of from about 1 $hr^{-1}$ to about 100 $hr^{-1}$ and an aromatic hydrocarbon/alkylating agent mole ratio of from about 1/1 to about 20/1.

(G) The alkylation of aromatic hydrocarbons, e.g., benzene, with long chain olefins, e.g., $C_{14}$ olefin. Typical reaction conditions include a temperature of from about 50° C. to about 200° C., a pressure of from about atmospheric to about 200 atmospheres, a weight hourly space velocity of from about 2 $hr^{-1}$ to about 2000 $hr^{-1}$ and an aromatic hydrocarbon/olefin mole ratio of from about 1/1 to about 20/1. The resulting products from the reaction are long chain alkyl aromatics which when subsequently sulfonated have particular application as synthetic detergents;

(H) The alkylation of aromatic hydrocarbons with light olefins to provide short chain alkyl aromatic compounds, e.g., the alkylation of benzene with propylene to provide cumene. Typical reaction conditions include a temperature of from about 10° C. to about 200° C., a pressure of from about 1 to about 30 atmospheres, and an aromatic hydrocarbon weight hourly space velocity (WHSV) of from 1 $hr^{-1}$ to about 50 $hr^{-1}$;

(I) The hydrocracking of heavy petroleum feedstocks, cyclic stocks, and other hydrocrack charge stocks. The zeolite catalyst system will contain an effective amount of at least one hydrogenation component of the type employed in hydrocracking catalysts.

(J) The alkylation of a reformate containing substantial quantities of benzene and toluene with fuel gas containing short chain olefins (e.g., ethylene and propylene) to produce mono- and dialkylates. Preferred reaction conditions include temperatures from about 100° C. to about 250° C., a pressure of from about 100 to about 800 psig, a WHSV -olefin from about 0.4 hr$^{-1}$ to about 0.8 hr$^{-1}$, a WHSV -reformate of from about 1 hr$^{-1}$ to about 2 hr$^{-1}$ and, optionally, a gas recycle from about 1.5 to 2.5 vol/vol fuel gas feed.

(K) The alkylation of aromatic hydrocarbons, e.g., benzene, toluene, xylene, and naphthalene, with long chain olefins, e.g., $C_{14}$ olefin, to produce alkylated aromatic lube base stocks. Typical reaction conditions include temperatures from about 160° C. to about 260° C. and pressures from about 350 to 450 psig.

(L) The alkylation of phenols with olefins or equivalent alcohols to provide long chain alkyl phenols. Typical reaction conditions include temperatures from about 100° C. to about 250° C., pressures from about 1 to 300 psig and total WHSV of from about 2 hr$^{-1}$ to about 10 hr$^{-1}$.

(M) The conversion of light paraffins to olefins and/or aromatics. Typical reaction conditions include temperatures from about 425° C. to about 760° C. and pressures from about 10 to about 2000 psig. Processes for preparing aromatic compounds from light paraffins are described in U.S. Pat. No. 5,258,563, which is hereby incorporated by reference.

(N) The conversion of light olefins to gasoline, distillate and lube range hydrocarbons. Typical reaction conditions include temperatures of from about 175° C. to about 375° C. and a pressure of from about 100 to about 2000 psig.

(O) Two-stage hydrocracking for upgrading hydrocarbon streams having initial boiling points above about 200° C. to premium distillate and gasoline boiling range products or as feed to further fuels or chemicals In a first stage, the catalyst comprising one or more catalytically active substances, e.g., a Group VIII metal, and the effluent from the first stage would be reacted in a second stage using a second catalyst comprising one or more catalytically active substances, e.g., a Group VIII metal, as the catalyst. Typical reaction conditions include temperatures from about 315° C. to about 455° C., a pressure from about 400 to about 2500 psig, hydrogen circulation of from about 1000 to about 10,000 SCF/bbl and a liquid hourly space velocity (LHSV) of from about 0.1 to 10;

(P) A combination hydrocracking/dewaxing process in the presence of the zeolite catalyst comprising a hydrogenation component and a zeolite such as zeolite Beta. Typical reaction conditions include temperatures from about 350° C. to about 400° C., pressures from about 1400 to about 1500 psig, LHSVs from about 0.4 to about 0.6 and a hydrogen circulation from about 3000 to about 5000 SCF/bbl.

(Q) The reaction of alcohols with olefins to produce mixed ethers, e.g., the reaction of methanol with isobutene and/or isopentene to provide methyl-t-butyl ether (MTBE) and/or t-amyl methyl ether (TAME). Typical conversion conditions include temperatures from about 20° C. to about 200° C., pressures from 2 to about 200 atm, WHSV (gram-olefin per hour gram-zeolite) from about 0.1 hr$^{-1}$ to about 200 hr$^{-1}$ and an alcohol to olefin molar feed ratio from about 0.1/1 to about 5/1.

(R) The disproportionation of aromatics, e.g., the disproportionation of toluene to make benzene and paraxylene. Typical reaction conditions include a temperature of from about 200° C. to about 760° C., a pressure of from about atmospheric to about 60 atmosphere (bar), and a WHSV of from about 0.1 hr$^{-1}$ to about 30 hr$^{-1}$.

(S) The conversion of naphtha (e.g., $C_6$–$C_{10}$) and similar mixtures to highly aromatic mixtures. Thus, normal and slightly branched chained hydrocarbons, preferably having a boiling range above about 40° C., and less than about 200° C., can be converted to products having a substantial higher octane aromatics content by contacting the hydrocarbon feed with the zeolite at a temperature in the range of from about 400° C. to 600° C., preferably 480° C. to 550° C. at pressures ranging from atmospheric to 40 bar, and liquid hourly space velocities (LHSV) ranging from 0.1 to 15.

(T) The adsorption of alkyl aromatic compounds for the purpose of separating various isomers of the compounds.

(U) The conversion of oxygenates, e.g., alcohols, such as methanol, or ethers, such as dimethylether, or mixtures thereof to hydrocarbons including olefins and aromatics with reaction conditions including a temperature of from about 275° C. to about 600° C., a pressure of from about 0.5 atmosphere to about 50 atmospheres and a liquid hourly space velocity of from about 0.1 to about 100;

(V) The oligomerization of straight and branched chain olefins having from about 2 to about 5 carbon atoms. The oligomers which are the products of the process are medium to heavy olefins which are useful for both fuels, i.e., gasoline or a gasoline blending stock, and chemicals. The oligomerization process is generally carried out by contacting the olefin feedstock in a gaseous state phase with a zeolite catalyst at a temperature in the range of from about 250° C. to about 800° C., a LHSV of from about 0.2 to about 50 and a hydrocarbon partial pressure of from about 0.1 to about 50 atmospheres. Temperatures below about 250° C. may be used to oligomerize the feedstock when the feedstock is in the liquid phase when contacting the zeolite catalyst. Thus, when the olefin feedstock contacts the catalyst in the liquid phase, temperatures of from about 10° C. to about 250° C. may be used.

(W) The conversion of $C_2$ unsaturated hydrocarbons (ethylene and/or acetylene) to aliphatic $C_{6-12}$ aldehydes and converting said aldehydes to the corresponding $C_{6-12}$ alcohols, acids, or esters.

In general, the catalytic conversion conditions include a temperature of from about 100° C. to about 760° C., a pressure of from about 0.1 atmosphere (bar) to about 200 atmospheres (bar), a weight hourly space velocity of from about 0.08 hr$^{-1}$ to about 2,000 hr$^-$.

The process of the present invention finds application in the vapor phase disproportionation of toluene. Such vapor phase disproportionation comprises contacting toluene under disproportionation conditions with the macrostructures comprising large pore or intermediate pore size zeolites to yield a product mixture which comprises a mixture of unreacted (unconverted) toluene and benzene and xylene. In the more preferred embodiment, the catalyst will be first selectivated prior to use in the disproportionation process. Processes for selectivating the catalyst are known to persons skilled in the art. For instance, selectivation may be accomplished by exposing the catalyst in a reactor bed to a thermally decomposable organic compound, e.g., toluene, at a temperature in excess of the decomposition temperature of said compound, e.g., from about 480° C. to about 650° C., more preferably 540° C. to 650° C., at a WHSV in the range of from about 0.1 to 20 lbs of feed per pound of catalyst per hour, at a pressure in the range of from about 1 to 100 atmospheres, and in the presence of 0 to about 2 moles of hydrogen, more preferably from about 0.1 to about 2 moles of hydrogen per mole of organic compound, and optionally in the presence of 0–10 moles of nitrogen or another inert gas per mole of organic compound. This process is conducted for a period of time until a sufficient quantity of coke has deposited on the catalyst surface, generally at least about 2% by weight and more preferably from about 8 to about 40% by weight of coke. In a preferred embodiment, such a selectivation process is conducted in the presence of hydrogen in order to prevent rampant formation of coke on the catalyst.

Selectivation of the catalyst can also be accomplished by treating the catalyst with a selectivation agent such as an organosilicon compound. The silica compounds may comprise polysiloxane including silicone and siloxanes, and a silane including disilanes and alkoxysilanes.

Silicone compounds that find particular application can be represented by the formula:

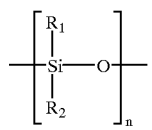

wherein $R_1$ is hydrogen, fluoride, hydroxy, alkyl, aralkyl, alkaryl or fluoro-alkyl. The hydrocarbon substituents generally contain from 1 to 10 carbon atoms and preferably are methyl or ethyl groups. $R_2$ is selected from the same group as $R_1$, and n is an integer of at least 2 and generally in the range of 2 to 1000. The molecular weight of the silicone compound employed is generally between 80 and 20,000 and preferably 150 to 10,000. Representative silicone compounds included dimethylsilicone, diethylsilicone, phenylmethylsilicone, methyl hydrogensilicone, ethylhydrogensilicone, phenylhydrogensilicone, methylethylsilicone, phenylethylsilicone, diphenylsilicone, methyltri fluoropropylsilicone, ethyltrifluoropropylsilicone, tetrachlorophenyl methyl silicone, tetrachlorophenylethyl silicone, tetrachloro phenylhydrogen silicone, tetrachlorophenylphenyl silicone, methylvinylsilicone and ethylvinylsilicone. The silicone compound need not be linear but may be cyclic as for example hexamethylcyclotrisiloxane, octamethylcyclotetrasiloxane, hexaphenyl cyclotrisiloxane and octaphenylcyclotetrasiloxane. Mixtures of these compounds may also be used as well as silicones with other functional groups.

Useful siloxanes or polysiloxanes include as non-limiting examples hexamethylcyclotrisiloxane, octamethylcyclotetrasiloxane, decamethyl cyclopentasiloxane, hexamethyldisiloxane, octamethyltrisiloxane, decamethyltetrasiloxane, hexaethylcyclotrisiloxane, octaethylcyclo tetrasiloxane, hexaphenylcyclotrisiloxane and octaphenylcyclo tetrasiloxane.

Useful silanes, disilanes, or alkoxysilanes include organic substituted silanes having the general formula:

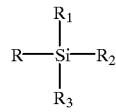

wherein R is a reactive group such as hydrogen, alkoxy, halogen, carboxy, amino, acetamide, trialkylsilyoxy, $R_1$, $R_2$, and $R_3$ can be the same as R or can be an organic radical which may include alkyl of from 1 to 40 carbon atoms, alkyl or aryl carboxylic acid wherein the organic portion of the alkyl contains 1 to 30 carbon atoms and the aryl group contains 6 to 24 carbon which may be further substituted, alkylaryl and arylalkyl groups containing 7 to 30 carbon atoms. Preferably, the alkyl group for an alkyl silane is between 1 and 4 carbon atoms in chain length.

When used for the vapor phase disproportionation of toluene, the catalytic macrostructures will preferably comprise aluminosilicate MFI-type zeolite having a silica to alumina mole ratio of from about 20 to about 200:1, preferably, 25:1 to about 120:1.

Once the catalyst has been selectivated to the desired degree, reactor selectivation conditions are changed to disproportionation conditions. Disproportionation conditions include a temperature between about 375° C. and 550° C., more preferably between about 400° C. and 485° C., at a hydrogen to toluene mole ratio of from 0 to about 10, preferably between about 0.1 and 5 and more preferably from about 0.1 to 1, at a pressure between about 1 atmosphere and 100 atmospheres and utilizing WHSV of between about 0.5 and 50.

The disproportionation process may be conducted as a batch, semi-continuous or continuous operation using a fixed or moving bed catalyst system deposited in a reactor bed. The catalyst may be regenerated after coke deactivation by burning off the coke to a desired extent in an oxygen-containing atmosphere at elevated temperatures as known in the art.

The process of the present invention also finds application in a process for isomerizing one or more xylene isomers in a Cg aromatic feed to obtain ortho-, meta-, and para-xylene in a ratio approaching the equilibrium value. In particular, xylene isomerization is used in conjunction with a separation process to manufacture para-xylene. For example, a portion of the para-xylene in a mixed $C_8$ aromatics stream may be recovered using processes known in the art, e.g., crystallization, adsorption, etc. The resulting stream is then reacted under xylene isomerization conditions to restore ortho-, meta-, and paraxylenes to a near equilibrium ratio. Ethylbenzene in the feed is either removed from the stream or is converted during the process to xylenes or to benzene which are easily separated by distillation. The isomerate is blended with fresh feed and the combined stream is distilled to remove heavy and light by-products. The resultant $C_8$ aromatics stream is then recycled to repeat the cycle.

In the vapor phase, suitable isomerization conditions include a temperature in the range 250° C.–600° C., preferably 300° C.–550° C., a pressure in the range 0.5–50 atm abs, preferably 10–25 atm abs, and a weight hourly space velocity (WHSV) of 0.1 to 100, preferably 0.5 to 50. Optionally, isomerization in the vapor phase is conducted in the presence of 0.1 to 30.0 moles of hydrogen per mole of alkylbenzene.

When use to isomerize feeds containing ethylbenzene, the catalytic macrostructure catalyst will preferably contain at least one hydrogenation metal. Examples of such metals include the oxide, hydroxide, sulfide, or free metal (i.e., zero valent) forms of Group VIII metals (i.e., Pt, Pd, Ir, Rh, Os, Ru, Ni, Co, and Fe), Group IVB metals (i.e., Sn and Pb), Group VB metals (i.e., Sb and Bi), and Group VIIA metals (i.e., Mn, Tc, and Re). Noble metals (i.e., Pt, Pd, Ir, Rh, Os, and Ru) are preferred. Combinations of catalytic forms of noble or non-noble metals, such as combinations of Pt with Ni, may be used. The valence state of the metal is preferably in a reduced valence state, e.g., when this component is in the form of an oxide or hydroxide. The reduced valence state of this metal may be attained, in situ, during the course of a reaction, when a reducing agent, such as hydrogen, is included in the feed to the reaction.

The amount of metal present in the zeolite catalyst will be an effective amount which will generally be from about 0.001 to about 10 percent by weight and, preferably 0.05 to 3.0 percent by weight.

The process of the present invention is useful for cracking a naphtha feed, e.g., $C_4^+$ naphtha feed, particularly a $C_4^-$ 290° C. naphtha feed to produce low molecular weight olefins, e.g., $C_2$ through $C_4$ olefins, particularly ethylene and propylene. Such a process is preferably carried out by contacting the naphtha feed at temperatures ranging from 500° C. to about 750° C., more preferably 550° C. to 675° C., at a pressure from subatmospheric up to 10 atmospheres, but preferably from about 1 atmosphere to about 3 atmospheres.

The process of the present invention is useful in the transalkylation of polyalkylaromatic hydrocarbons. Examples of suitable polyalkylaromatic hydrocarbons include di-, tri-, and tetra-alkyl aromatic hydrocarbons, such as diethylbenzene, triethylbenzene, diethylmethylbenzene (diethyl-toluene), diisopropyl-benzene, triisopropylbenzene, diisopropyltoluene, dibutylbenzene, and the like. Preferred polyalkylaromatic hydro-carbons are the dialkyl benzenes. Particularly preferred polyalkyl-aromatic hydrocarbons are diisopropylbenzene and diethylbenzene.

The feed used in the transalkylation process will preferably have a molar ratio of aromatic hydrocarbon to polyalkylaromatic hydrocarbon of preferably from about 0.5:1 to about 50:1, and more preferably from about 2:1 to about 20:1. The reaction temperature will preferably range from about 340° C. to 500° C. to maintain at least a partial liquid phase, and the pressure will be preferably in the range of about 50 psig to 1,000 psig, preferably 300 psig to 600 psig. The weight hourly space velocity will range from about 0.1 to 10.

The process of the present invention is also useful for converting aromatic compounds from paraffins. Example of suitable paraffins including aliphatic hydrocarbons containing 2 to 12 carbon atoms. The hydrocarbons may be straight chain, open or cyclic and may be saturated or unsaturated. Example of hydrocarbons include propane, propylene, n-butane, n-butenes, isobutane, isobutene, and straight- and branch-chain and cyclic pentanes, pentenes, hexanes, and hexenes.

The aromatization conditions include a temperature of from about 200° C. to about 700° C., a pressure of from about 0.1 atmosphere to about 60 atmospheres, a weight hourly space velocity (WHSV) of from about 0.1 to about 400 and a hydrogen/hydrocarbon mole ratio of from about 0 to about 20.

The catalytic macrostructure used in the aromatization process preferably comprises large crystals of an intermediate pore size zeolite such a MFI type zeolite (example ZSM-5). The catalyst preferably contains gallium. Gallium may be incorporated into the during synthesis of the zeolite or it may be exchanged or impregnated or otherwise incorporated into the zeolite after synthesis. Preferably, 0.05 to 10, and most preferably 0.1 to 2.0 wt. % gallium is associated with the catalyst.

EXAMPLES

In the examples, the resulting products were evaluated by a scanning electron microscope (SEM), X-ray diffractometry (XRD), spectroscopy and by measurements of the specific surface area and pore size distribution with krypton or nitrogen adsorption.

Scanning electron microscope studies were conducted on samples coated with gold (by a sputtering technique). A scanning electron microscope of the Philips XL 30 type with a Lanthanum hexa-Boride emission source was used in these studies.

X-ray diffraction studies were conducted with a Siemens D-5000 powder diffractometer.

Nitrogen adsorption measurements to determine specific surface area and particle size distribution were carried out with an ASAP 2010 from Micromeritics Instruments, Inc.

Elemental analysis concerning carbon, nitrogen and hydrogen was carried out on certain samples by means of an analytical instrument from LECO Corporation (LECO CHN-600). The particle size and particle size distribution for the colloidal suspensions of discrete microcrystals of molecular sieves used as starting material according to the process were determined by dynamic light scattering (ZetaPlus, Brookhaven Instruments).

Example 1

Macrostructures comprising spherical particles of porous amorphous silica with very high specific surface area were prepared as follows:

A synthesis solution with the following composition (on a molar basis): $9TPAOH:25SiO_2:480H_2O:100EtOH$ (TPAOH representing tetrapropylammonium hydroxide and EtOH representing ethanol) was prepared by mixing 20.0 grams of tetraethoxysilane (>98%), 34.56 grams of tetrapropylammonium hydroxide (1.0M solution) and 5.65 grams of distilled water. The mixture was allowed to hydrolyze in a polyethylene flask on a shaking table for 12 hours at room temperature. An amount of 1.0 grams of a strongly basic anion exchange resin sold under the tradename Dowex 1X2-100 type and manufactured by the Dow Chemical Company was added to 10 grams of the synthesis solution. The anion exchange resin was present as spherical particles with a particle size range of 50–100 mesh (dry) and the ion exchange capacity of the resin was specified by the manufacturer to be 3.5 mEq/g.

The mixture of ion exchanger and synthesis solution was heated in a polyethylene reactor equipped with a reflux condenser in an oil bath at 100° C. for 48 hours. After this time, the ion exchanger resin particles were separated from the solution by filtration and treated in a 0. 1M ammonia solution in an ultrasound bath for 15 minutes and then separated from the ammonia solution by filtration. Next, the particles were washed three times by suspension in distilled water, followed by separation by filtration, and then dried in a heating cabinet at 60° C. for 12 hours. Next, the particles were calcined at 600° C. in air for 4 hours, after heating to this temperature at a rate of 10° C./min.

The resulting material consisted of hard, solid, white spherical particles with a size distribution identical to that in the employed ion exchanger. Elemental analysis showed that the particles were almost entirely free of carbon, hydrogen and nitrogen, which showed that the ion exchanger had been completely eliminated in the calcining stage.

Figure 2:
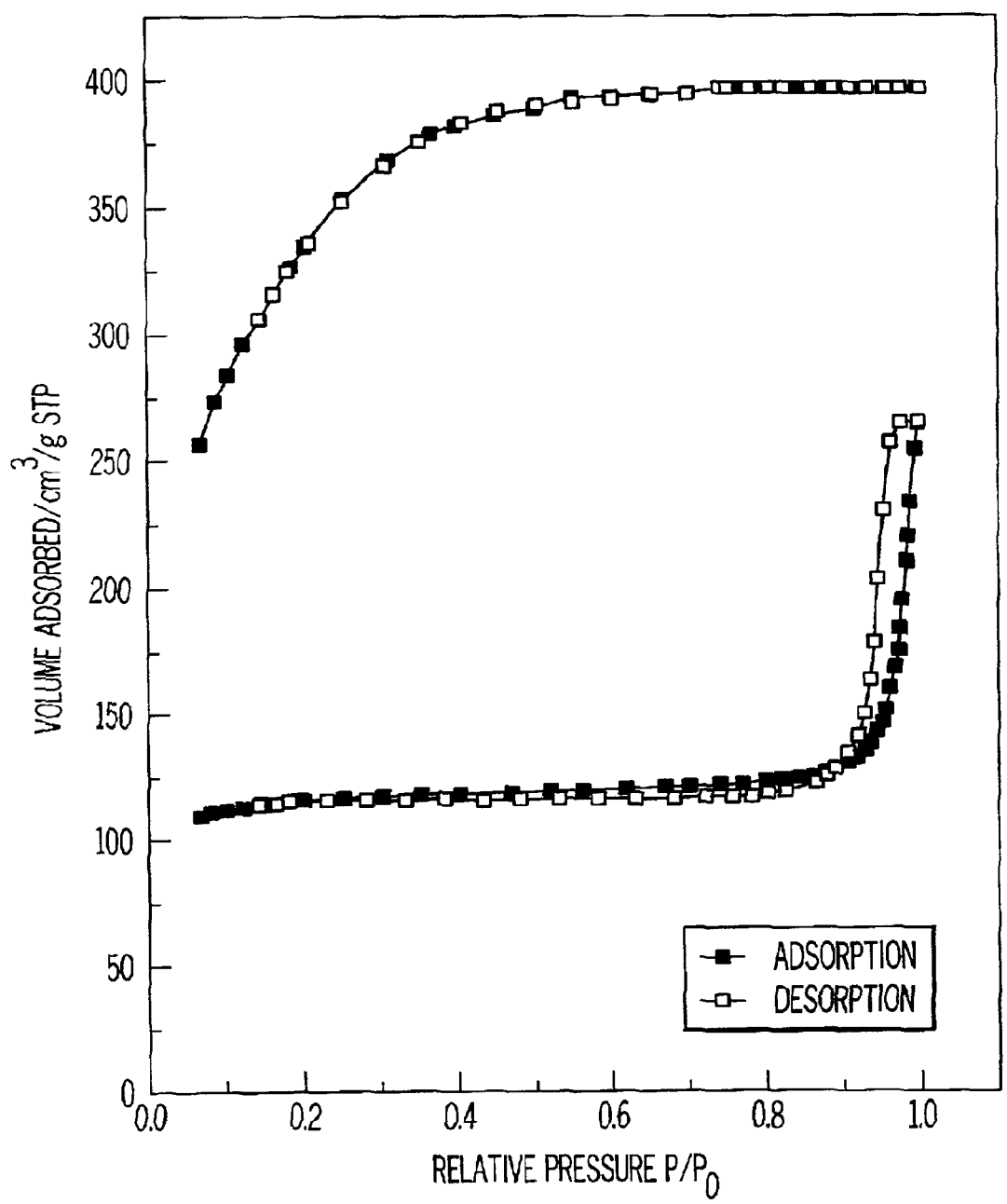
FIG. 2 represents adsorption-desorption isotherms measured for spherical particles of amorphous silica of Examples 1 and 2.

X-ray diffractometry also showed that the material was completely amorphous. The particles were also analyzed by nitrogen adsorption measurements at the boiling point of nitrogen to determine the specific surface area, the adsorption isotherm and pore size distribution of the porous amorphous silica. The specific surface area was calculated from the adsorption data according to the BET equation as 1220 m$^2$/g. The recorded isotherm is shown in FIG. 2 and was of type I, which is typical of porous materials. Calculation of the pore size distribution by the BJH method (desorption isotherm) showed that a very small fraction (about 20 m$^2$/g) of the total specific surface area of the material was found in pores in the mesopore range (diameter >20 Å). The average pore diameter was calculated at 9.5 Å by the Horvath-Kawazoes method.

Example 2

Macrostructures comprising spherical particles of amorphous aluminum silicate with high specific surface area in pores in both the micro- and mesopore range were prepared as follows:

25 grams of a synthesis solution with the molar composition: 2.4Na$_2$O:1.0TEACl:0.4Al$_2$O$_3$:10SiO$_2$:/460H$_2$O (TEACl representing tetraethylammonium chloride) were added to 2.0 grams of a strongly basic ion exchanger sold under the tradename Dowex MSA-1 and manufactured by the Dow Chemical Company (particle size 20–50 mesh and [dry] ion exchange capacity of 4 mEq/g) in a polyethylene reactor. The synthesis mixture was prepared by first dissolving 0.75 grams sodium aluminate (50.6 wt % Al$_2$O$_3$, 36 wt % Na$_2$O) in 35 grams of a 1M NaOH solution at 100° C. This solution was then added to a mixture of 40 grams distilled water, 1.66 grams TEACl and 15 grams silica sol (Bindzil 40/130, Eka Chemicals AB, solids content 41.36 wt %, 0.256 wt % Na$_2$O) during agitation for 2 hours. The mixture of ion exchanger and synthesis solution was treated in a polyethylene reactor equipped with a reflux condenser in an oil bath at 100° C. for 48 hours. After this time, the ion exchanger particles were separated from the solution by filtration and treated in a 0.1M ammonia solution in an ultrasound bath for 15 minutes and then separated from the ammonia solution by filtration. The particles were finally washed three times by suspension in distilled water, followed by separation by filtration, and then dried in a heating cabinet at 60° C. for hours. Next, the particles were calcined at 600° C. in air for 4 hours, after heating to this temperature at a rate of 10° C./min.

Visual inspection and analysis with a scanning electron microscope showed that the resulting material consisted of very hard, solid, white spherical particles with size distribution identical to that in the employed ion exchanger. Elemental analysis showed that the particles were almost entirely free of carbon, hydrogen and nitrogen, which showed that the ion exchanger material had been completely eliminated in the calcining stage.

X-ray diffractometry showed that the material was completely amorphous. The particles were further analyzed by nitrogen adsorption measurements at the boiling point of nitrogen to determine the specific surface area, adsorption isotherms and pore size distribution. The specific surface area was calculated from the adsorption data according to the BET equation as 594 m$^2$/g. The recorded isotherm is shown in Example 2 and was of type IV. Calculation of the pore size distribution by the BJH method (desorption isotherm) showed that a relatively large percentage of the total (cumulative) pore volume (about 65%) was found in pores in the mesopore range (radius >20 Å).

Example 3

Macrostructures comprising spherical particles of Silicalite 1 were prepared as follows:

14.3 grams of a synthesis solution with the molar composition: 9TPAOH:25SiO$_2$:480H$_2$O:100EtOH were added to 1.0 grams of a macroporous strongly basic ion exchanger sold under the tradename Dowex MSA-1 and manufactured by the Dow Chemical Company (particle size 20–50 mesh [dry]; ion exchange capacity: 4 mEq/g). The synthesis mixture was prepared as described in Example 1. The mixture of ion exchanger and synthesis solution was heated in a polyethylene reactor equipped with a reflux condenser in an oil bath at 100° C. for 48 hours. After this time, the ion exchanger particles were separated from the solution and the material was crystallized in the bulk phase by filtration and treated in a 0.1M ammonia solution in an ultrasound bath for 15 minutes, whereupon they were separated again by filtration. Next, the particles were washed three times by suspension in distilled water, followed by separation by filtration, and then dried in a heating cabinet at 60° C. for 12 hours. Next, the particles were calcined at 600° C. in air for 10 hours, after heating to this temperature at a rate of 1° C./min.

Figure 3:
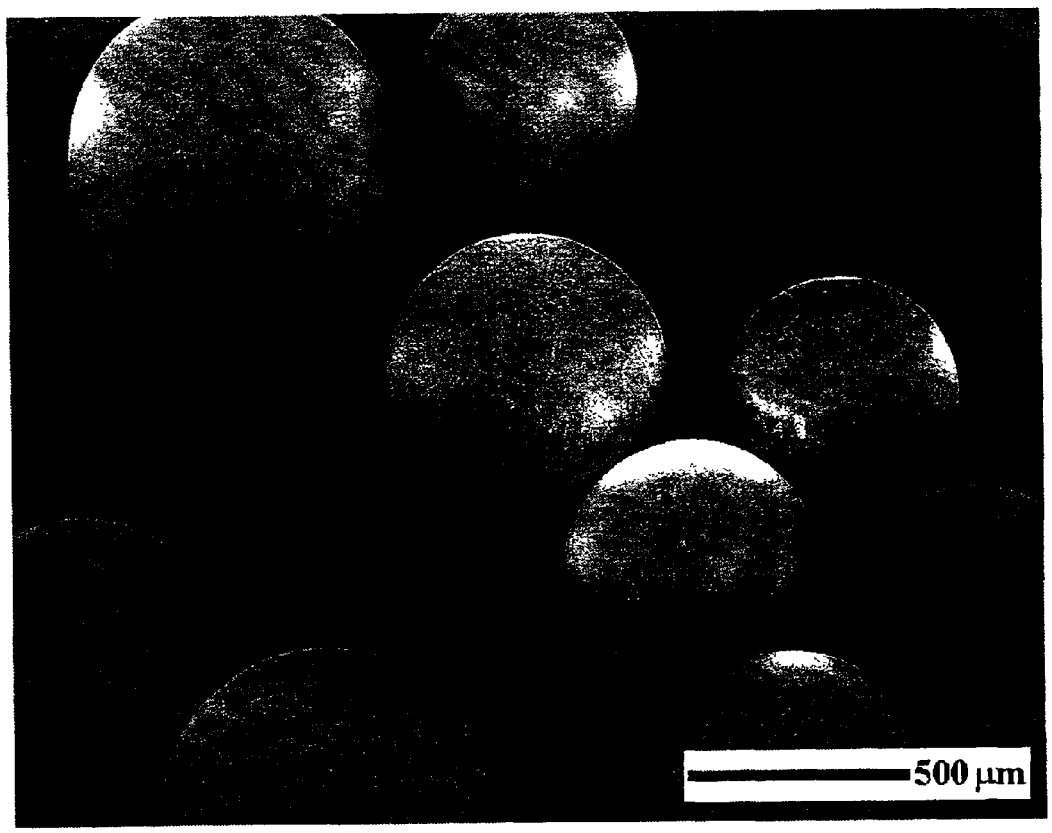
FIG. 3 and FIG. 4 show SEM micrographs, at two different magnifications, of spherical particles of the molecular sieve Silicalite 1 of Example 3.
Figure 4:
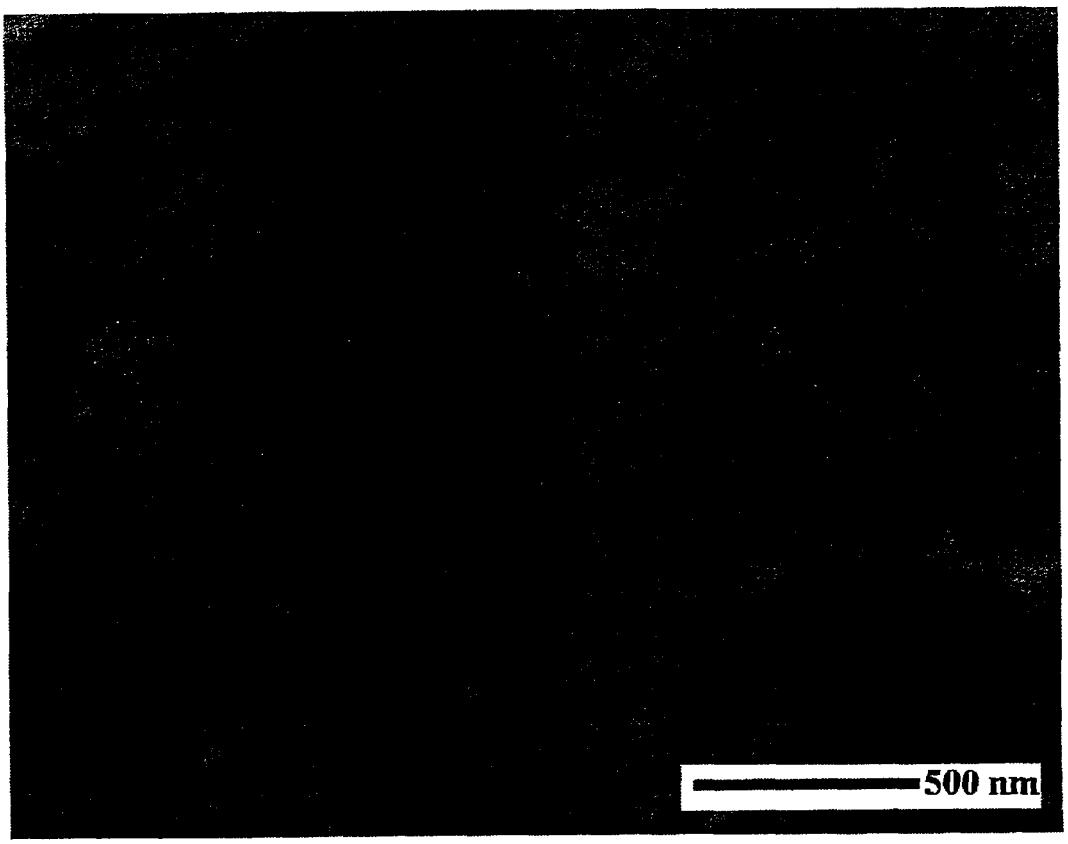
Figure 5:
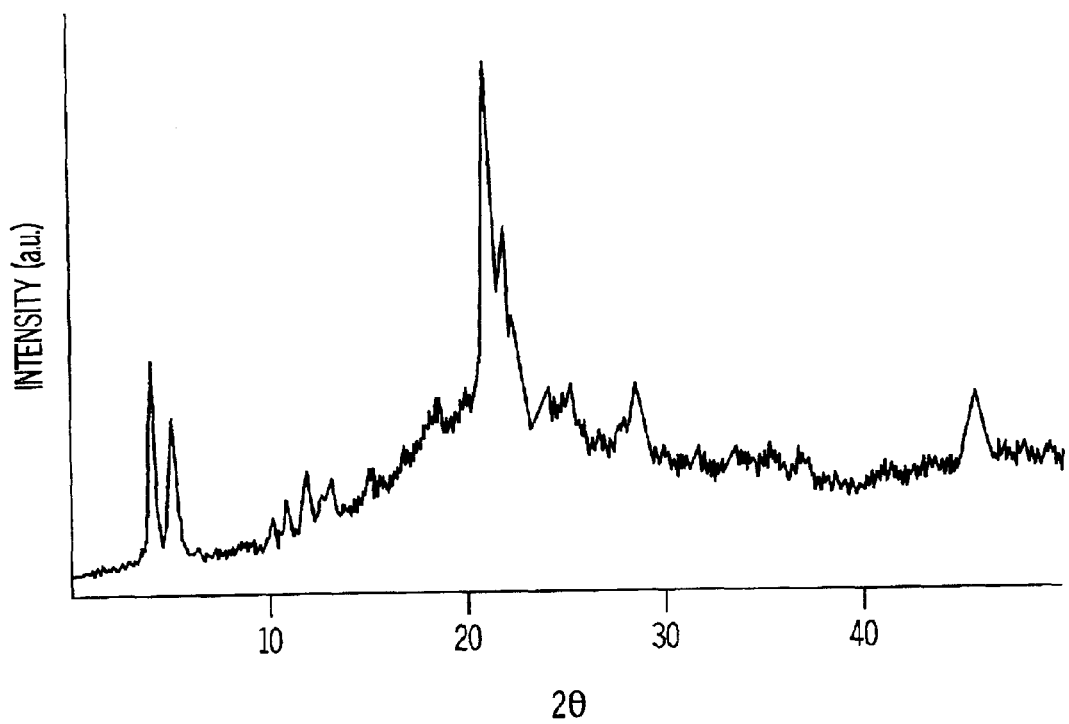
FIG. 5 represents an X-ray diffraction pattern for spherical particles of the molecular sieve Silicalite 1 of Example 3.
Figure 6:
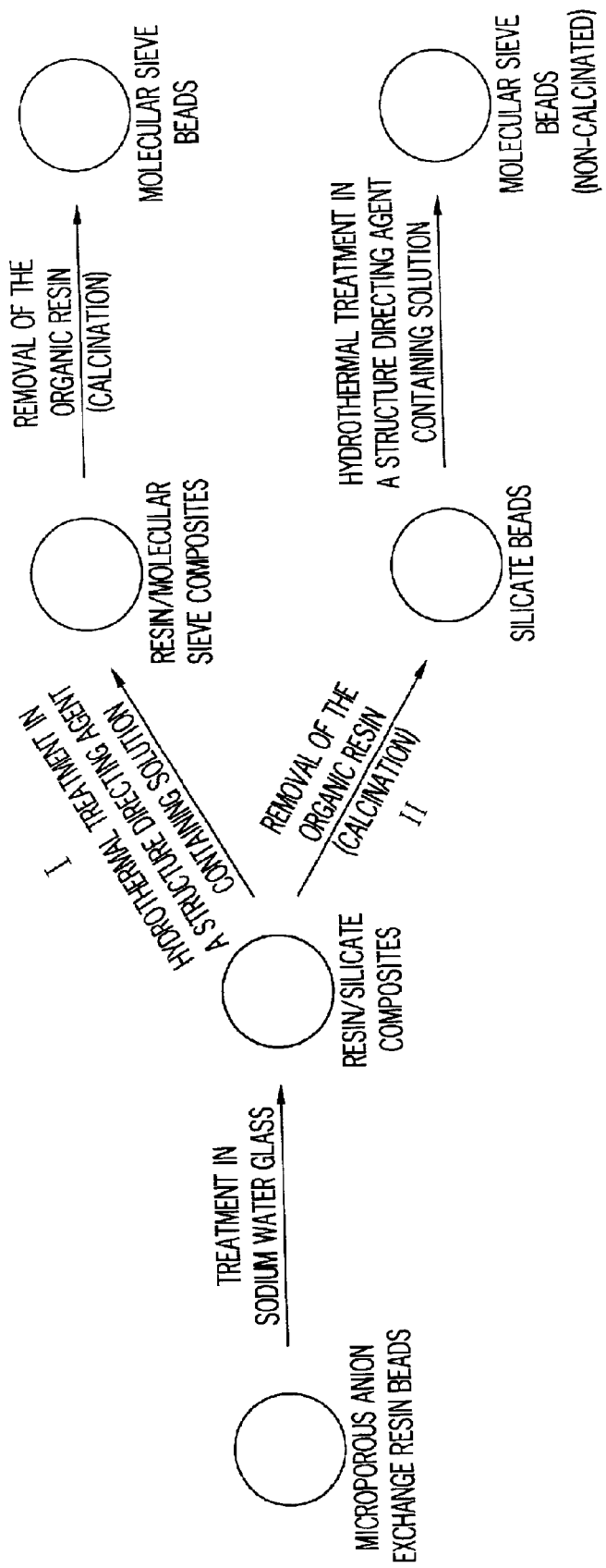
FIG. 6 represents a schematic description of the different stages in production of spherical particles or thin films of an amorphous metal oxide composite which either before or after removal of the organic ion exchanger is then converted by hydrothermal treatment in the presence of a structure directing agent into a macrostructure composed of particles of a zeolite and/or molecular sieve composition.

Visual inspection and scanning electron microscopy revealed that the resulting material consisted of very hard, solid (homogeneous), white spherical particles with a size distribution identical to that in the employed ion exchanger. The primary particles making up the spheres had a size of about 100 nm. Also, the primary particles on the surface of the spheres was similar to the particles in the interior of the spheres. Elemental analysis showed that the particles were almost entirely free of carbon, hydrogen and nitrogen, which showed that the ion exchanger material was fully eliminated in the calcining stage. FIGS. 3 and 4 are two SEM photographs of the material taken at two different magnifications. FIG. 3 taken at the lower magnification shows the spherical character of the particles, whereas FIG. 4 taken at high magnification shows the presence of small primary particles (primary crystals) with a size of about 100 nm. X-ray diffractometry revealed that the material is crystalline and consists of Silicalite 1, but that it also contains a percentage of amorphous material. An X-ray diffraction pattern for this sample is shown in FIG. 5. Analysis with nitrogen adsorption gave a specific surface area of 438 m$^2$/g and showed that most of the pore volume was found in micropores with an average pore diameter of 6 Å, calculated according to the Horvath-Kawazoes method.

Silicalite 1 was prepared using the same procedures as described above, except that the hydrothermal treatment was carried out at different temperatures.

In the first Silicalite 1 preparation, the hydrothermal treatment temperature was 165° C. Scanning electron microscopy showed that the surface of the spheres of the resulting product were overlaid with crystals of MFI-type zeolite and had a size up to 500 nm. The inner part of the spheres was less homogeneous and agglomerates of small particles could be distinguished.

In the second preparation, the hydrothermal treatment was carried out in two steps. The temperature of the first step was 100° C. and the temperature of the second step was at 165° C. The resulting spheres were highly crystalline which indicates that the degree of crystallinity can be increased by a second hydrothermal treatment at a higher temperature.

Example 4

Macrostructures comprising spherical particles of ZSM-5 were prepared as follows:

15 grams of a synthesis solution with the molar composition: 0.35 $Na_2O$:9TPAOH:0.25$Al_2O_3$:25 $SiO_2$:405$H_2O$ were added to 1.0 grams of a macroporous strongly basic anion exchanger sold under the tradename Dowex MSA-1 and manufactured by the Dow Chemical Company (particle size 20–50 mesh [dry]; ion exchange capacity: 4 mEq/g). The synthesis mixture was prepared by first dissolving 0.408 grams of aluminum isopropoxide in 10 grams of 1.0M tetrapropylammonium hydroxide. Another solution was prepared by dissolving 6.0 grams freeze-dried silica sol (Bindzil 30/220, 31 wt % $SiO_2$, 0.5 wt % $Na_2O$ Eka Chemicals, AB) in 26 grams 1.0M TPAOH at 100° C. The two solutions were mixed under agitation for 30 minutes. The mixture of ion exchanger and synthesis solution was heated in a polyethylene reactor equipped with a reflux condenser in an oil bath at 100° C. for 20 days. After this time, the ion exchanger particles were separated from the solution and the material was crystallized in the bulk phase by filtration and treated in a 0.1M ammonia solution in an ultrasound bath for 15 minutes, and then separated again by filtration. Next, the particles were washed three times by suspension in distilled water, followed by separation by filtration, and then dried in a heating cabinet at 60° C. for 12 hours. Next, the particles were calcined at 600° C. in air for 10 hours, after heating to this temperature at a rate of 1° C./min.

Visual inspection and analysis with a scanning electron microscope showed that the product largely consisted of white, solid particles with a size and shape identical to that of the employed ion exchanger. A relatively large fraction of the product, however, was shown to consist of particles with roughly the same size as the employed ion exchanger, but with a more irregular shape. SEM analysis at high magnification showed that the particles consisted of intergrown crystals with a morphology typical of MFI structures and with a size of about 1 μm. X-ray diffractometry showed that the particles consisted of zeolite ZSM-5 and a relatively large fraction of amorphous material. The specific surface area was measured by nitrogen adsorption at 612 $m^2$/g.

Example 5

Macrostructures comprising spherical particles of zeolite A were prepared as follows:

18.0 grams of a synthesis solution with the molar composition: 0.22 $Na_2O$:5.0 $SiO_2$:$Al_2O_3$:8 $TMA_2O$:/400$H_2O$ were added to 1.0 grams of a strongly basic anion exchanger sold under the tradename Dowex MSA-1 and manufactured by the Dow Chemical Company. The synthesis mixture was prepared by first dissolving 1.25 grams of aluminum isopropoxide and 9.0 grams tetramethylammonium hydroxide pentahydrate in 0.90 grams of 1.0M solution of NaOH and 3.0 grams water under agitation for 2 hours. This solution was added to a mixture of 3.0 grams silica sol (Bindzil 30/220, 31 wt % $SiO_2$, 0.5 wt % $Na_2O$ Eka Chemicals, AB) and 12 grams of distilled water and the resulting solution was agitated for 3 hours. The mixture of ion exchanger and synthesis solution was heated in a polyethylene reactor equipped with a reflux condenser in an oil bath at 100° C. for 10 hours. After this time, the ion exchanger particles were separated from the solution and the material was crystallized in the bulk phase by filtration and treated in a 0.1M ammonia solution in an ultrasound bath for 15 minutes, and then separated again by filtration. Next, the particles were washed three times by suspension in distilled water, followed by separation by filtration, and then dried in a heating cabinet at 60° C. for 12 hours. Next, the particles were calcined at 600° C. in air for 10 hours, after heating to this temperature at a rate of 1° C./min.

Visual inspection and analysis by scanning electron microscopy showed that the product largely consisted of light brown, solid particles. The size of the particles was smaller than the employed ion exchanger. A smaller fraction of the product consisted of fragmented particles. SEM at high magnification showed that the particles are homogeneous and are constructed from intergrown primary particles with a size up to about 300 nm. X-ray diffractometry showed that the resulting material contained zeolite A and a certain amount of amorphous material. Nitrogen adsorption measurements gave a specific surface area (according to the BET equation) of 306 m 2/g and indicated the presence of both micro- and mesoporosity.

Example 6

Macrostructures comprising spherical particles of zeolite Beta were prepared as follows:

15 grams of a synthesis solution with the molar composition: 0.35 $Na_2O$:9TEAOH:0.5$Al_2O_3$:25 $SiO_2$:295$H_2O$ were added to 1.0 grams of a strongly basic anion exchanger sold under the tradename Dowex MSA-1 and manufactured by the Dow Chemical Company. The synthesis mixture was prepared by dissolving 0.81 grams aluminum isopropoxide in 6.0 grams tetraethylammonium hydroxide (TEAOH, 20% solution) at 100° C. This solution was added to a solution of 6.0 grams freeze-dried silica sol (Bindzil 30/220, 31 wt % $SiO_2$, 0.5 wt % $Na_2O$ Eka Chemicals, AB) dissolved in 20 grams of TEAOH (20% solution) and the resulting solution was agitated for 30 minutes. The mixture of ion exchanger and synthesis solution was heated in a polyethylene reactor equipped with a reflux condenser in an oil bath at 100° C. for 8 days. After this time, the ion exchanger particles were separated from the solution and the material was crystallized in the bulk phase by filtration and treated in a 0.1M ammonia solution in an ultrasound bath for 15 minutes, whereupon the particles were separated again by filtration. The particles were finally washed three times by suspension in distilled water, followed by separation by filtration, and then dried in a heating cabinet at 60° C. for 12 hours. Next, the particles were calcined at 600° C. in air for 10 hours, after heating to this temperature at a rate of 1° C./min.

Visual inspection, as well as analysis with a scanning electron microscope, showed that the product largely consisted of hard, white, solid particles with a size and shape identical to that of the employed ion exchanger. SEM analysis at high magnification shows that the material is constructed of intergrown primary particles with a size of about 80 μm. X-ray diffractometry showed that the particles contained zeolite Beta as the only crystalline phase. The specific surface area calculated with the BET equation, based on nitrogen adsorption data, was 580 $m^2$/g.

Example 7

A film of Silicalite 1 was built upon the surface of a macrostructure of Silicalite 1 produced according to Example 3 as follows:

10.0 grams of synthesis solution with the composition and preparation according to Example 3 were added to 0.20 grams of calcined product produced according to Example 3. This mixture was heated at 100° C. in a polyethylene reactor equipped with a reflux condenser for 48 hours. After this time, the particles were separated from the solution and the material was crystallized in the bulk phase by filtration and treated in a 0.1M ammonia solution in an ultrasound bath for 15 minutes, whereupon they were separated again by filtration. The particles were finally washed three times by suspension in distilled water, followed by separation by filtration, and then dried in a heating cabinet at 60° C. for 12 hours. Part of the material was calcined at 600° C. for 10 hours, after heating to this temperature at a rate of 1° C./min. X-ray diffraction measurements on the calcined sample revealed that the sample contained Silicalite 1 as the only crystalline phase. Scanning electron microscopy detected an outer layer of Silicalite 1 on the surface of the particles, a layer that synthesis had built up from about 300/-nm large primary particles. The specific surface area was determined for the uncalcined sample as 92 m$^2$/g, whereas the corresponding value measured for the calcined sample was 543 m$^2$/g. The difference in the surface before and after calcining indicates that the outer shell of Silicalite 1 effectively encloses the open pore system in the original particles.

Example 8

30g of sodium water glass (21.4 wt. % SiO$_2$, 6.7 wt. % Na$_2$O, 0.024 wt. % Al$_2$O$_3$, Akzo Nobel) were added to 3 g of a macroporous strongly basic ion exchange resin (Dowex MSA-1) in a polyethylene reactor. The reactor was subsequently submerged in a silicon oil bath preheated to 100° C. and treated under reflux for 4 hours (initially, all resin beads were floating on the surface of the water glass; the treatment was discontinued when all the particles sank). Afterwards, the resin beads were separated, treated in a 0.1 M NH$_3$ solution in an ultrasonic bath for 5 minutes, washed several times by suspension in distilled water and dried at 60° C. for two hours.

1 g each of the as prepared resin-sodium silicate composites were mixed with 20 g of 2% and 5%, respectively, TPAOH aqueous solutions in a PTFE-lined stainless steel autoclave. The mixtures were then hydrothermally treated at 170° C. for 24 h. After the treatment, the beads were separated, treated in a 0.1 M NH$_3$ solution in an ultrasonic bath for 5 minutes, washed several times by suspension in distilled water and dried at 60° C. Finally, the organic resin was removed by calcination at 600° C. for 5 hours after heating to that temperature at a heating rate of 1° C./min.

Figure 7:
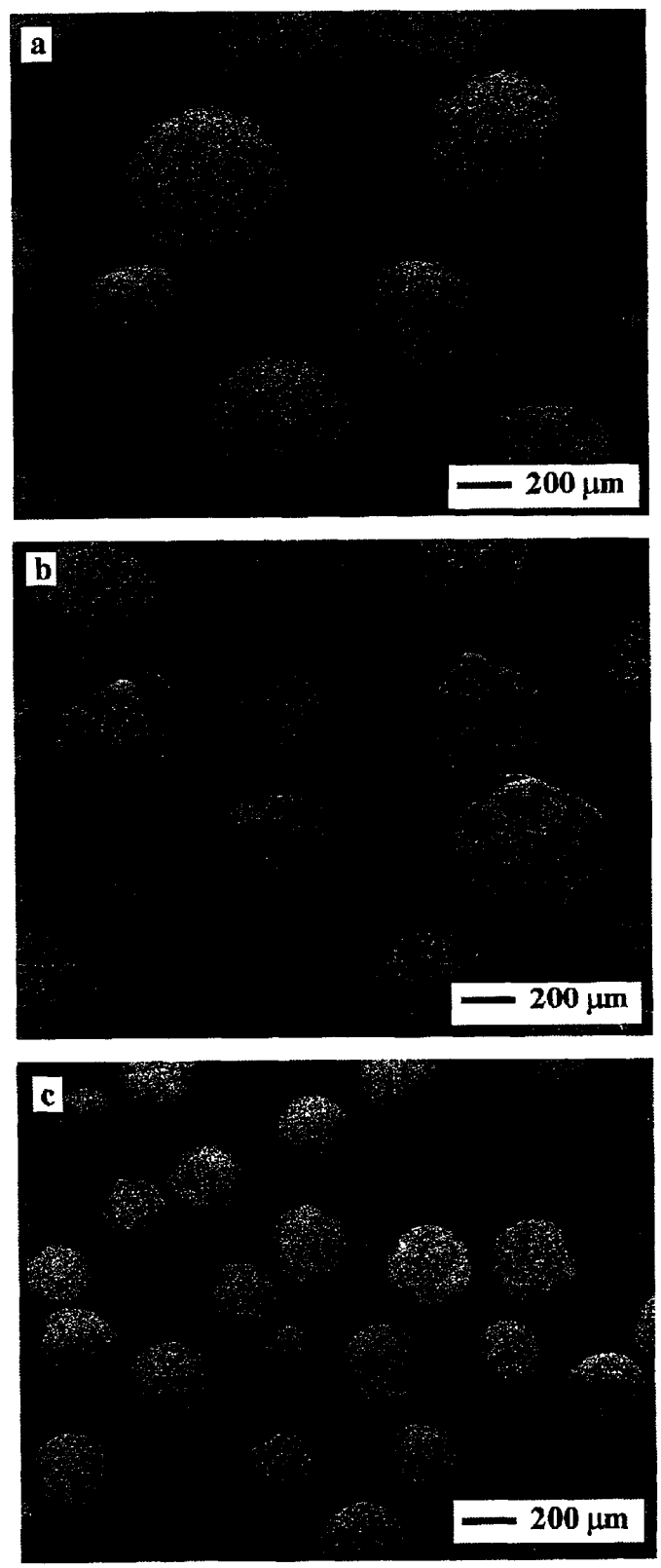
FIG. 7 shows SEM micrographs of the calcined products prepared according to the invention.
Figure 8:
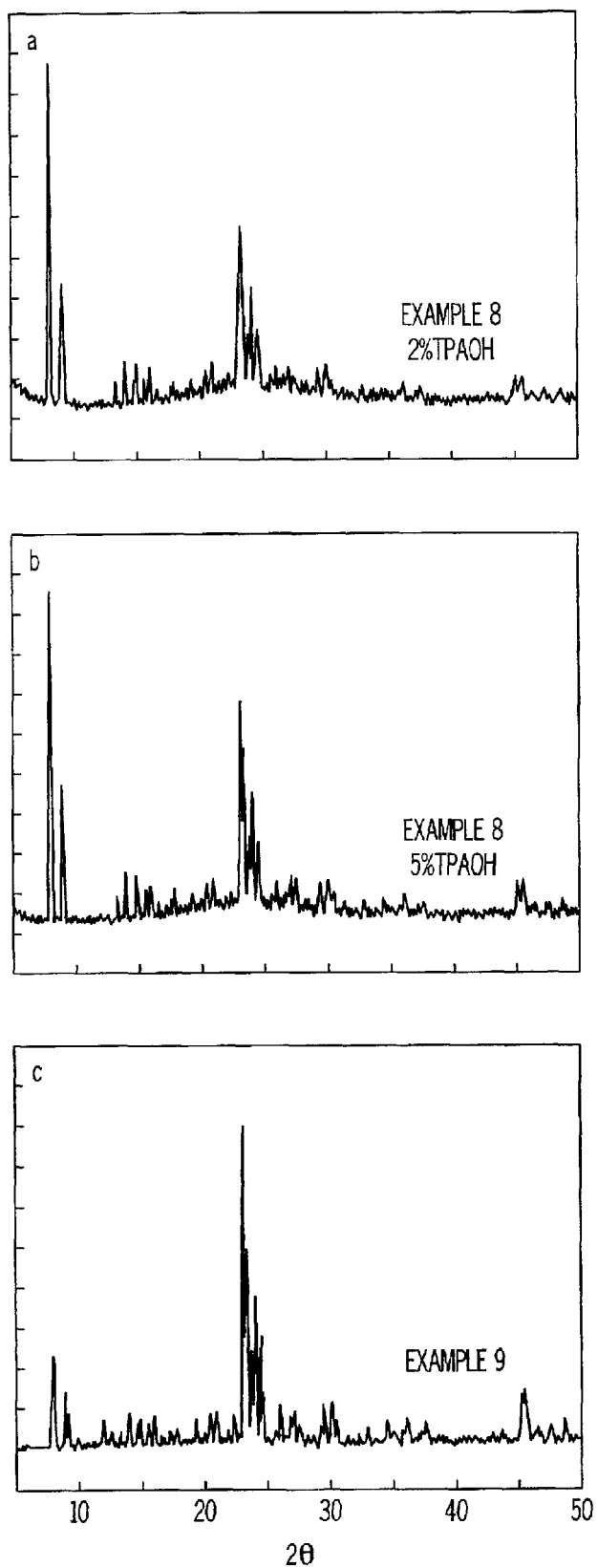
FIG. 8 represents XRD patterns of the calcined products prepared according to the invention.

FIG. 7 shows SEM micrographs of the calcined products prepared using (a) 2% TPAOH and (b) 5% TPAOH. The corresponding XRD patterns are shown in FIGS. 8a and b. BET surface area values for the calcined particles prepared with 2 and 5% TPAOH solutions were 1112 and 730 m$^2$/g, respectively.

The particles shrunk upon calcination and this shrinkage was more pronounced when 5% TPAOH solutions were used. As seen from the XRD patterns the products consist of silicalite-1 together with a certain amount of amorphous material in both samples and this amount was higher when 2% TPAOH solution was used. The presence of amorphous material was confirmed by the very high BET surface area values.

Example 9

30 g of sodium water glass (21.4 wt. % SiO$_2$, 6.7 wt. % Na$_2$O, 0.024 wt. % Al$_2$O$_3$, Akzo Nobel) were added to 3 g of a macroporous strongly basic ion exchange resin (Dowex MSA-1) in a polyethylene reactor. The reactor was subsequently submerged in a silicon oil bath preheated to 100° C. and treated under reflux for 4 hours (initially, all resin beads were floating on the surface of the water glass; the treatment was discontinued when all the particles sank). Afterwards, the resin beads were separated, treated in a 0.1 M NH$_3$ solution in an ultrasonic bath for 5 minutes, washed several times by suspension in distilled water and dried at 60° C. for two hours.

The as prepared particles were calcined at 600° C. for 5 hours after heating to that temperature at a heating rate of 1° C./min. Elementary analysis after the calcining showed that the sample contained 95.6 wt. % SiO$_2$ and 1.03 wt. % Na$_2$O. 1 g of the calcined particles was hydrothermally treated with 10 g of 5% TPAOH aqueous solution at 170° C. for 24 h. After the treatment, the particles were separated, treated in a 0.1 M NH$_3$ solution in an ultrasonic bath for 5 minutes, washed several times by suspension in distilled water and dried at 60° C. for two hours.

SEM micrographs of the particles obtained after the treatment in TPAOH containing solution are shown in FIG. 7c and the corresponding XRD pattern—in FIG. 8c. The BET surface area was 10 m$^2$/g (the TPA cations were present in the silicalite-1 structure).

The particles were shrunk considerably upon calcination. No amorphous material was detected by XRD and nitrogen adsorption measurements.

Example 10

30 g of sodium water glass (21.4 wt. % SiO$_2$, 6.7 wt. % Na$_2$O, 0.024 wt. % Al$_2$O$_3$, Akzo Nobel) were added to 3g of a macroporous strongly basic ion exchange resin (Dowex MSA-1) in a polyethylene reactor. The reactor was subsequently submerged in a silicon oil bath preheated to 100° C. and treated under reflux for 4 hours (initially, all resin beads were floating on the surface of the water glass; the treatment was discontinued when all the particles sank). Afterwards, the resin beads were separated, treated in a 0.1 M NH$_3$ solution in an ultrasonic bath for 5 minutes, washed several times by suspension in distilled water and dried at 60° C. for two hours.

1 g each of the as prepared particles were respectively hydrothermally treated with 20 g of 2 and 5% TPABr (Merck) solution at 170° C. for 24 h. After the treatment, the particles were separated, treated in a 0.1 M NH$_3$ solution in an ultrasonic bath for 5 minutes, washed several times by suspension in distilled water and dried at 60° C. for 5 hours after heating to that temperature at a heating rate of 1° C./min.

Figure 9:
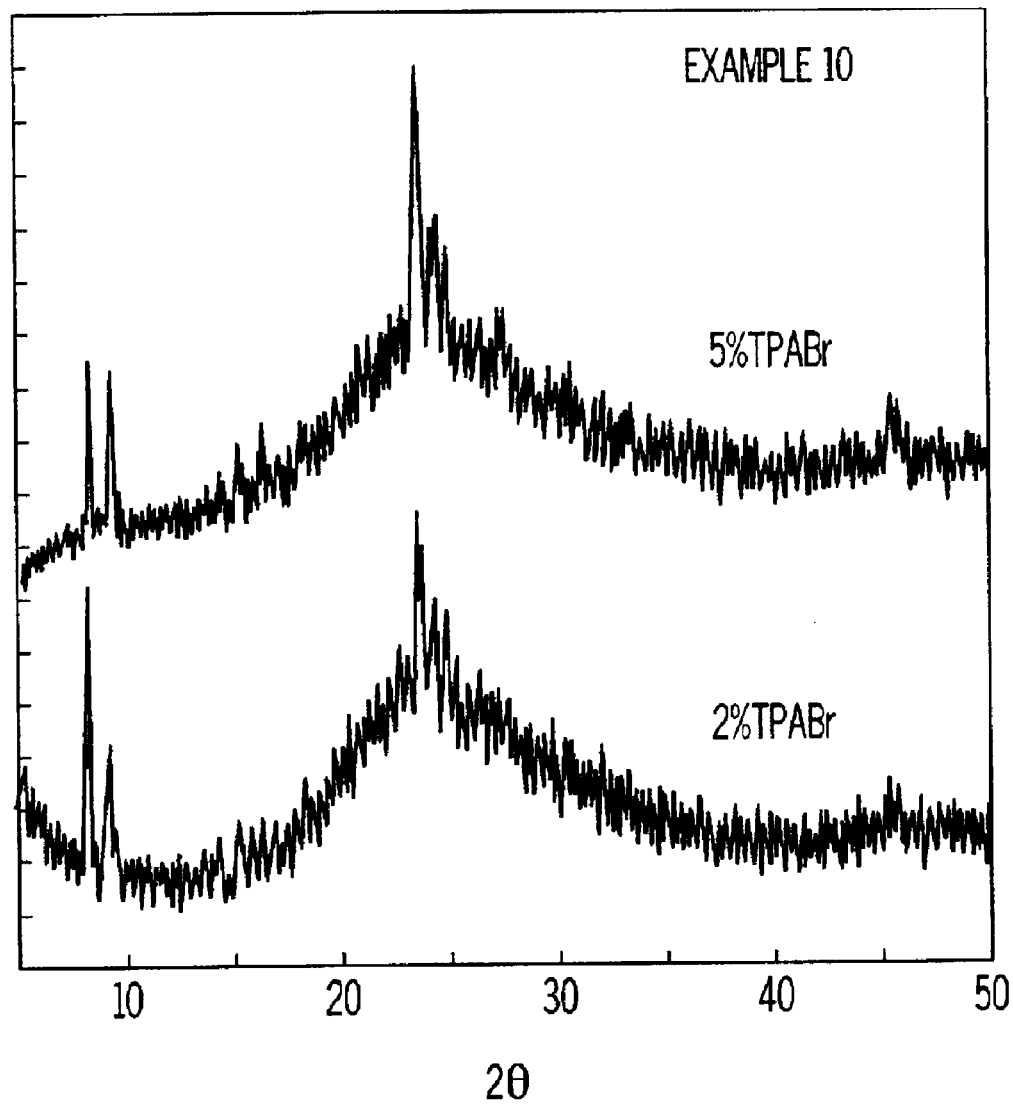
FIG. 9 represents XRD pattern of the calcined product prepared according to Example 10.

The particles shrunk upon calcination and were similar to the ones shown in FIG. 7a. XRD patterns of calcined samples prepared using 2% and 5% TPABr solutions are shown in FIG. 9. The diffrectograms show that both samples contain a significant amount of amorphous material in addition to silicalite-1. BET surface areas of the 2% and 5% samples were 1122 and 1098 m$^2$/g, respectively.

While the present invention has been described and illustrated by reference to particular embodiment thereof, it will be appreciated by those of ordinary skill in the art that the invention lends itself to variations not necessarily illustrated herein. For these reason, then, reference should be made solely to the appended claims for the purposes of determining the true scope of the present invention.

What is claimed is:

1. A process for preparing macrostructures comprised of a crystalline molecular sieve composition, comprising the steps of:

(a) forming a composite material composed of a porous organic ion exchanger having a three-dimensional pore structure and a continuous matrix of a mesoporous inorganic material within the three-dimensional pore structure of the porous organic ion exchanger; and (b) removing the porous organic ion exchanger from the composite material to yield the macrostructures (c) treating said continuous three-dimensional matrix of mesoporous inorganic material, before or after removal of said porous organic ion exchanger from the composite material, under hydrothermal conditions to convert at least a portion of said mesoporous inorganic material to a crystalline molecular sieve composition.

2. The process recited in claim 1, wherein the step of treating said continuous three-dimensional matrix of mesoporous inorganic material under hydrothermal conditions is conducted in the presence of a structuring agent to convert at least a portion of said mesoporous inorganic material to a crystalline molecular sieve composition.

3. The process recited in claim 1, wherein the step of treating under hydrothermal conditions occurs before the step of removing the porous organic ion exchanger from the composite material.

4. The process recited in claim 1, wherein the step of treating under hydrothermal conditions occurs after the step of removing the porous ion organic exchanger from the composite material.

5. The process recited in claim 1, wherein said macrostructures have a size and shape of the three-dimensional pore structure of said porous organic ion exchanger.

6. The process recited in claim 5, wherein said porous organic ion exchanger is a porous organic anionic ion exchanger.

7. The process recited in claim 6, wherein said porous anionic ion-exchanger has an ion-exchange capacity greater than about 1 meg./gm of dry weight of porous anionic ion-exchanger.

8. The process recited in claim 7, wherein said porous anionic ion-exchanger is a strongly basic anion-exchange resin containing quartenary ammonium groups.

9. The process recited in claim 8, wherein said porous organic ion exchanger is a polymer-based organic ion exchanger.

10. The process recited in claim 1, wherein said porous organic ion exchanger is a macroreticular ionic exchanger.

11. The process recited in claim 1, wherein said macrostructures have at least one dimension greater than about 0.1 mm.

12. The process recited in claim, wherein said macrostructures are spherical or cylindrical.

13. The process recited in claim 1, wherein said molecular sieve is an aluminosilicate zeolite or a metallosilicate substantially free of aluminum.

14. The process recited in claim 1, wherein said molecular sieve is a large pore size molecular sieve or an intermediate pore size molecular sieve.

15. The process recited in claim 1, wherein said molecular sieve is of a structure type selected from the group consisting of LTL, FAU, MOR, *BEA, MFI, MEL, MTW, MTT, MFS, FER, and TON.

16. The process recited in claim 1, wherein said molecular sieve is selected from the group consisting of zeolite A, zeolite L, zeolite X, zeolite Y, mordenite, zeolite beta, ZSM-5, ZSM-11, ZSM-22, ZSM-35, silicalite 1 and silicalite 2.

17. The process recited in claim 16, wherein said crystalline molecular sieve is a ZSM-5 or silicalite 1.

18. The process recited in claim 1, wherein said mesoporous inorganic material is selected from the group consisting of silica, aluminum silicate, and alumina.

19. The process recited in claim 18, wherein the mesoporous inorganic material is amorphous silica or amorphous silica-alumina having a specific surface area exceeding 200 $m^2/g$.

20. The process recited in claim 1, wherein said porous organic ion exchanger is removed by either an oxidation process or by dissolution.

* * * * *